US009668699B2

United States Patent
Georgescu et al.

(10) Patent No.: US 9,668,699 B2
(45) Date of Patent: Jun. 6, 2017

(54) METHOD AND SYSTEM FOR ANATOMICAL OBJECT DETECTION USING MARGINAL SPACE DEEP NEURAL NETWORKS

(71) Applicant: SIEMENS HEALTHCARE GMBH, Erlangen (DE)

(72) Inventors: Bogdan Georgescu, Plainsboro, NJ (US); Yefeng Zheng, Princeton Junction, NJ (US); Hien Nguyen, Princeton, NJ (US); Vivek Kumar Singh, Monmouth Junction, NJ (US); Dorin Comaniciu, Princeton Junction, NJ (US); David Liu, Franklin Park, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 14/709,536

(22) Filed: May 12, 2015

(65) Prior Publication Data

US 2015/0238148 A1    Aug. 27, 2015

Related U.S. Application Data

(63) Continuation-in-part of application No. 14/516,163, filed on Oct. 16, 2014.

(Continued)

(51) Int. Cl.
*A61B 5/00* (2006.01)
*G06T 7/00* (2017.01)
(Continued)

(52) U.S. Cl.
CPC .......... *A61B 5/7267* (2013.01); *G06K 9/4628* (2013.01); *G06K 9/6255* (2013.01);
(Continued)

(58) Field of Classification Search
CPC . A61B 5/7267; A61B 5/7275; A61B 19/5225; A61B 2019/5236;
(Continued)

(56) References Cited

U.S. PATENT DOCUMENTS

| 8,700,552 B2 | 4/2014 | Yu et al. |
| 2008/0085050 A1* | 4/2008 | Barbu .................. G06K 9/6292 382/154 |

(Continued)

FOREIGN PATENT DOCUMENTS

| EP | 3057510 | 8/2016 |
| WO | 2014072861 A3 | 5/2014 |
| WO | 2015058044 | 4/2015 |

OTHER PUBLICATIONS

Ghesu et al., Marginal Space Deep Learning: Efficient Architecture for Detection in Volumetric Image Data, Medical Image Computing and Computer-Assisted Intervention—MICCAI 2015, vol. 9349 of the series Lecture Notes in Computer Science pp. 710-718, Nov. 18, 2015.*
Bengio et al. 2012, Unsupervised Feature Learning and Deep Learning: A Review and New Perspectives, Jun. 24, 2012.*
Ghesu et al., Marginal Space Deep Learning: Efficient Architecture for Volumetric Image Parsing, IEEE Transactions on Medical Imaging, vol. 35, No. 5, May 2016.*

(Continued)

*Primary Examiner* — Bo J Peng

(57) ABSTRACT

A method and system for anatomical object detection using marginal space deep neural networks is disclosed. The pose parameter space for an anatomical object is divided into a series of marginal search spaces with increasing dimensionality. A respective deep neural network is trained for each of the marginal search spaces, resulting in a series of trained deep neural networks. Each of the trained deep neural networks can evaluate hypotheses in a current parameter space using discriminative classification or a regression function. An anatomical object is detected in a medical image by sequentially applying the series of trained deep neural networks to the medical image.

57 Claims, 15 Drawing Sheets

Related U.S. Application Data

(60) Provisional application No. 62/148,273, filed on Apr. 16, 2015, provisional application No. 62/121,782, filed on Feb. 27, 2015, provisional application No. 61/891,920, filed on Oct. 17, 2013.

(51) Int. Cl.
| | |
|---|---|
| *G06K 9/46* | (2006.01) |
| *G06K 9/62* | (2006.01) |
| *G06T 7/73* | (2017.01) |
| *G06T 7/77* | (2017.01) |
| *A61B 6/00* | (2006.01) |
| *A61B 8/08* | (2006.01) |
| *A61B 8/00* | (2006.01) |
| *A61B 5/055* | (2006.01) |

(52) U.S. Cl.
CPC ............... *G06T 7/0012* (2013.01); *G06T 7/73* (2017.01); *G06T 7/77* (2017.01); *A61B 5/055* (2013.01); *A61B 6/503* (2013.01); *A61B 6/507* (2013.01); *A61B 6/5217* (2013.01); *A61B 6/563* (2013.01); *A61B 8/0883* (2013.01); *A61B 8/0891* (2013.01); *A61B 8/5223* (2013.01); *A61B 8/565* (2013.01); *G06K 2209/051* (2013.01); *G06T 2207/10081* (2013.01); *G06T 2207/10088* (2013.01); *G06T 2207/10101* (2013.01); *G06T 2207/10132* (2013.01); *G06T 2207/20081* (2013.01); *G06T 2207/20084* (2013.01); *G06T 2207/30048* (2013.01); *G06T 2207/30104* (2013.01)

(58) Field of Classification Search
CPC ...... A61B 2019/524; A61B 2019/5276; G06T 7/0014; G06T 7/004; G06T 2207/20084
See application file for complete search history.

(56) References Cited

U.S. PATENT DOCUMENTS

| | | | |
|---|---|---|---|
| 2012/0232386 A1* | 9/2012 | Mansi | A61B 8/0883 600/437 |
| 2013/0138436 A1 | 5/2013 | Yu et al. | |
| 2013/0138589 A1 | 5/2013 | Yu et al. | |
| 2014/0072213 A1 | 3/2014 | Paiton et al. | |
| 2014/0100451 A1 | 4/2014 | Tolkowsky et al. | |
| 2015/0112182 A1 | 4/2015 | Sharma et al. | |
| 2015/0125049 A1 | 5/2015 | Taigman et al. | |
| 2015/0161987 A1 | 6/2015 | Horesh et al. | |
| 2015/0161988 A1 | 6/2015 | Dognin et al. | |
| 2015/0170002 A1 | 6/2015 | Szegedy et al. | |
| 2015/0245775 A1 | 9/2015 | Fonte et al. | |

OTHER PUBLICATIONS

Gustavo Carneiro et al: "Multiple dynamic models for tracking the left ventricle of the heart from ultrasound data using particle filters and deep learning architectures", 2010 IEEE Conference on Computer Vision and Pattern Recognition (CVPR), San Francisco, CA, USA, IEEE, Piscataway, NJ, USA, pp. 2815-2822, XP031725842, ISBN: 978-1-4244-6984-0 / 13.06.2010.

"Four-Chamber Heart Modeling and Automatic Segmentation for 3D Cardiac CT Volumes Using Marginal Space Learning and Steerable Features", Yefeng Zheng, Adrian Barbu, Bogdan Georgescu, Michael Scheuering, and Dorin Comaniciu; Zheng et al., "Four-Chamber Heart Modeling and Automatic Segmentation for 3D Cardiac CT Volumes Using Marginal Space Learning and Steerable Features", IEEE Trans. on Medical Imaging, vol. 27, No. 11, pp. 1668-1681, 2008.

Deng, Three Classes of Deep Learning Architectures and Their Applications: A Tutorial Survey, APSIPA Transactions of Signal and Information Processing, 2012, 28 pages.

Krizhevsky, et al., ImageNet Classification with Deep Convolutional Neural Networks, Conference: Advances in Neural Information Processing Systems 25, 2012, pp. 1-9.

* cited by examiner

METHOD AND SYSTEM FOR ANATOMICAL OBJECT DETECTION USING MARGINAL SPACE DEEP NEURAL NETWORKS

This application claims the benefit of U.S. Provisional Application No. 62/148,273, filed Apr. 16, 2015, and U.S. Provisional Application No. 62/121,782, filed Feb. 27, 2015, and is a continuation-in-part of U.S. application Ser. No. 14/516,163, filed Oct. 16, 2014, which claims the benefit of U.S. Provisional Application No. 61/891,920, filed Oct. 17, 2013, the disclosures of which are herein incorporated by reference.

BACKGROUND OF THE INVENTION

The present invention relates to anatomical object detection in medical image data, and more particularly, to anatomical object detection in medical image data using deep neural networks.

Fast and robust anatomical object detection is a fundamental task in medical image analysis that supports the entire clinical imaging workflow from diagnosis, patient stratification, therapy planning, intervention, and follow-up. Automatic detection of an anatomical object is a prerequisite for many medical image analysis tasks, such as segmentation, motion tracking, and disease diagnosis and quantification. Marginal space learning (MSL) was previously introduced to address the problem of anatomy detection and tracking in medical images, such as computed tomography (CT), magnetic resonance (MR), ultrasound, and fluoroscopic images. MSL is an efficient discriminative learning framework that typically uses handcrafted image features extracted from training images to train discriminative classifiers for anatomical object detection in a supervised manner. MSL works well for detecting anatomical structures in various two-dimensional (2D) and three-dimensional (3D) medical imaging modalities. However, anatomical object detection using MSL is not always robust, especially for some challenging detection problems in which the anatomical objects exhibit large variations in anatomy, shape, or appearance in the medical images

BRIEF SUMMARY OF THE INVENTION

The present disclosure provides methods and systems for anatomical object detection using marginal space deep neural networks. Embodiments of the present invention divide a parameter space of a target anatomical object into a series of marginal search spaces with increasing dimensionality. A respective deep neural network is trained for each of the marginal search spaces based on annotated training data. Instead of using handcrafted image features, each of the deep neural networks directly inputs image patches from the training data and learns high-level domain-specific image features. The trained deep neural network for a particular marginal search space may be discriminative, in that it calculates, for a given hypothesis in the search space, a probability that the hypothesis in the search space is correct, or may provide a regression function (regressor) that calculates, for each hypothesis in the search space, a difference vector from that hypothesis to predicted pose parameters of the object in the search space. Once the series of deep neural networks is trained, the trained deep neural networks can be applied to an input medical image to detect the target anatomical object in the input medical image.

DETAILED DESCRIPTION

Figure 1:
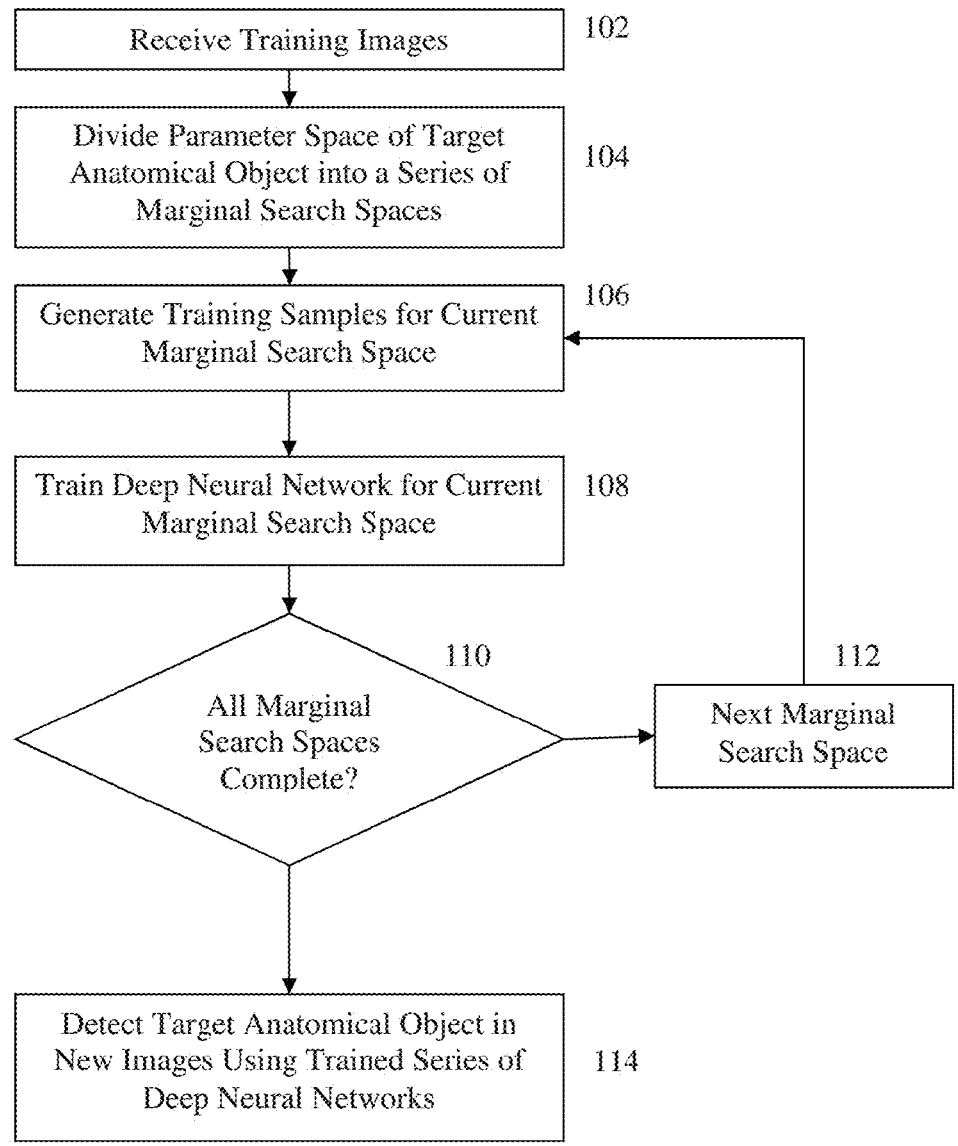
FIG. 1 illustrates a method of training a series of deep neural networks for anatomical object detection in medical images according to an embodiment of the present invention.

The present invention relates to methods and systems for anatomical object detection using marginal space deep neural networks. Embodiments of the present invention are described herein to give a visual understanding of the machine learning based methods for anatomical object detection. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Marginal Space Learning (MSL) is an efficient discriminative learning framework that can be used for anatomical object detection and tracking in medical images, such as but not limited to computed tomography (CT), magnetic resonance imaging (MRI), ultrasound, and X-ray fluoroscopy. MSL exploits large image databases with expert annotations to train discriminative classifiers in a supervised manner on marginal feature distributions from positive (object) and negative (non-object) training samples. Classifiers are sequentially trained by gradually increasing the dimensionality of the search space and focusing only on positive distribution regions. MSL efficiently deals with the problem of an exponentially increasing number of hypotheses relative to the dimensionality of the parameter space. Given a new image the input parameter space is sequentially searched with the trained classifiers to find the correct anatomical object location. MSL is typically implemented using handcrafted image features, such as Haar wavelet features for object position estimation and steerable features for position-orientation estimation and position-orientation-scale estimation. Even though such features are efficient, their classification power is weak. MSL relies on boosting technology, for example using a probabilistic boosting tree (PBT), to integrate a large number of weak features into a strong classifier. Although MSL works well for detecting many anatomical structures in various 2D or 3D medical imaging modalities, when the appearance of an anatomical object is complex relative to the parameter space or when there is a large degree of ambiguity between the background and the anatomical object of interest, there are still problems in capturing these distributions in the discriminative MSL framework with the standard image features.

Embodiments of the present invention utilize deep neural networks trained directly on the image data instead of handcrafted features extracted from the image data to learn complex image patterns and detect anatomical objects based on the complex image patterns. Deep neural networks are machine learning based neural networks with multiple hidden layers of learned features or variables between the input data and the output data. Deep neural networks will typically be implemented with three or more hidden layers. Deep neural networks are typically used in direct multi-class classification scenarios and are not typically applied to anatomical object detection tasks because the extension of deep neural networks to the task of anatomical object detection can be quite computationally complex due to the need to scan a large image parameter space, especially for large 2D+time or 3D volumetric images. Embodiments of the present invention provide computationally efficient methods for utilizing deep neural networks for anatomical object detection in medical images.

FIG. 1 illustrates a method of training a series of deep neural networks for anatomical object detection in medical images according to an embodiment of the present invention. The method of FIG. 1 utilizes a database of training images to train a series of deep neural networks in a series of marginal search spaces of increasing dimensionality to determine a full pose parameter space for an anatomical object in a medical image. In a possible implementation, the method of FIG. 1 can train each of the deep neural networks to be discriminative in that it calculates, for a given hypothesis in a search space, a probability that the hypothesis in the search space is correct. In another possible implementation, the method of FIG. 1 can train each of the deep neural networks to be a regression function (regressor) that calculates, for each hypothesis in a search space, a difference vector from that hypothesis to predicted pose parameters of the target anatomical object in the search space. It is also possible, the one or more of the deep neural networks can be discriminative and one or more of the deep neural networks can be a regressor.

Referring to FIG. 1, at step 102, training images are received. In particular, a plurality of training images are loaded from a database. The training images can be 2D or 3D medical images acquired using any medical imaging modality, such as but not limited to CT, MRI, Ultrasound, X-ray fluoroscopy, DynaCT, etc. At least a subset of the training images are annotated with the pose (e.g., position, orientation, and scale) of the target anatomical object. The training images may also include non-annotated images as well.

At step 104, a parameter space of the target anatomical object is divided into a series of marginal search spaces. The target object annotated in the training images is parameterized and the parameter space of the target anatomical object is divided into a series of marginal search spaces with increasing dimensionality. For example, a set of parameters for a target anatomical object can be the rigid position (translation), orientation (rotation), and scale defining the pose of the object in an image, and the parameter space of the target anatomical object can be divided into marginal search spaces of position, postion+orientation, and position+orientation+scale. A range for each of the parameter spaces is determined from the annotated training images. The parameter space for the target object in 2D images has five degrees of freedom (two for position, one for orientation, and two for anisotropic scaling), while the parameter space for the target object in 3D images has nine degrees of freedom (three for position, three for orientation, and three for anisotropic scaling). For 2D images, the full parameter space can be expressed as $(x,y,\theta,s_x,s_y)$, where $(x,y)$ denotes a center position of the target anatomical object, $\theta$ denotes an orientation or rotation of the anatomical object, and $(s_x,s_y)$ denotes of scale of the anatomical object in the x and y directions, and the parameter space can be divided into the following marginal search spaces: $(x,y)$, $(x,y,\theta)$, and $(x,y,\theta,s_x,s_y)$. For 3D images, the full parameter space can be expressed as $(x,y,z,\theta_x,\theta_y,\theta_z,s_x,s_y,s_z)$, where $(x,y,z)$ denotes a center position of the target anatomical object, $(\theta_x,\theta_y,\theta_z)$ denotes the orientation of the anatomical object, and $(s_x,s_y,s_z)$ denotes of scale of the anatomical object, and the parameter space can be divided into the following marginal search spaces: $(x,y,z)$, $(x,y,z,\theta_x,\theta_y,\theta_z)$, and $(x,y,z,\theta_x,\theta_y,\theta_z,s_x,s_y,s_z)$. Instead of training a deep neural network to directly detect the target object in the full parameter space, the method of FIG. 1 sequentially trains a series of deep neural networks to detect the parameters of the target anatomical object by training a respective deep neural network in each of the marginal search spaces.

At step 106, training samples are generated for the current marginal search space. The training samples are image patches that are used as hypotheses in the current search space to train the deep neural network for that search space. For the first search space (e.g., position) the training samples are generated by selecting image patches from the training images. For training a discriminative deep neural network, ground truth image patches for the first search space are selected as positive training samples and random non-ground-truth image patches are selected as negative training samples. For example, in the case in which the first marginal search space is the position of the target anatomical objects, image patches centered at the ground truth center position of the target anatomical object in each annotated training image are selected as positive training samples and one or more random image patches located more than a predetermined distance (e.g., 5 mm) from the ground truth center position of the target anatomical object are randomly selected from each annotated training image as the negative training samples. For training the deep neural network as a regressor, the training samples (hypotheses) for the first search space are image patches selected from the range of the first search space in the training images. For subsequent marginal search spaces, the training samples for the current search space are generated by evaluating training samples from the preceding search space using the trained deep neural network for the preceding search space to determine a number of candidates in the preceding search space, and then augmenting the candidates selected by the trained deep neural network in the preceding search space with the additional parameters of the current search space sampled from a range of the current search space in the training images.

At step 108, a deep neural network is trained for the current marginal search space. In a possible embodiment, the deep neural network for the current search space may be a discriminative deep neural network that image patches of an image as hypotheses and for each image patch calculates a probability the parameters of the image patch for the current search space are the parameters for the target anatomical object in the current search space. In another possible implementation, the first deep neural network may train a regressive function that inputs image patches of an image as hypotheses and calculates a difference vector for each input image patch between the parameters of the image patch in the current search space and the parameters of the target anatomical object in the current search space, resulting in predicted parameters of the target anatomical object in the current search space.

At step 110, it is determined if the training for all marginal search spaces is complete. If the training for all of the marginal search spaces is not complete, the method proceeds to step 112. If the training for all of the marginal search spaces is complete the method proceeds to step 114. At step 112, the method proceeds to the next marginal search space and then returns to step 106 and repeats steps 106, 108, and 110. In particular, when the method returns to step 106, the hypotheses in the previous search space are evaluated using the deep neural network trained for the previous search space to determine candidates in the previous search space, and training samples (hypotheses) for the next search space are generated by augmenting the candidates in the previous search space with additional parameters for the next search space. The deep neural network for the next search space is then trained, and these steps are repeated until a respective deep neural network is trained for each of the marginal search spaces. The final deep neural network will detect the anatomical object in the full parameter space. For example, steps 108 and 110 can be repeated to train a first deep neural network to detect the position of a target anatomical object, train a second deep neural network to detect position and orientation of the target anatomical object, and train a third deep neural network to detect position, orientation, and scale of the anatomical object. At step 114, once the training is complete for all of the marginal spaces, the series of trained deep neural networks can be used to detect an anatomical object in a new image. Steps 102-112 can be performed offline in a training stage and then the series of trained deep neural networks can be stored in a memory or storage of a computer system, and step 114 can be performed when a new image is received using the stored series of trained deep neural networks. When a new image is received, anatomical object detection can be performed by inputting image patches of the new image into the first trained deep neural network and then processing the image patches sequentially through the series of trained deep neural networks.

Figure 2:
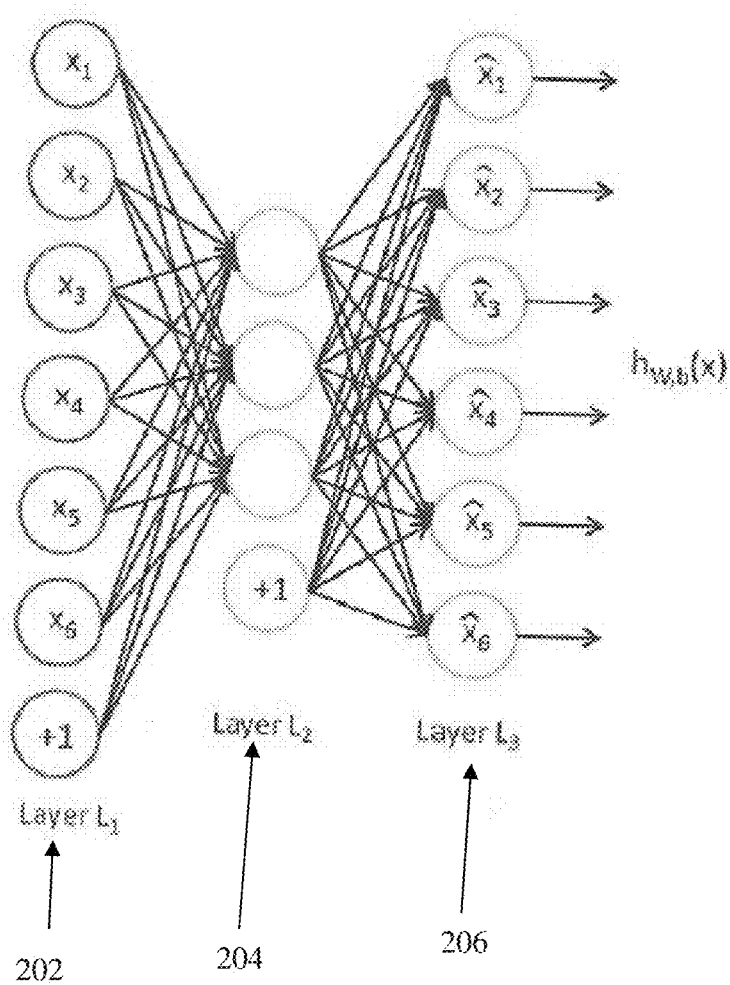
FIG. 2 illustrates an exemplary auto-encoder neural network.

In a first embodiment, the method of FIG. 1 can be used to train a series of discriminative deep neural networks, each of which calculates, for a given hypothesis in its marginal search space, a probability that the hypothesis in the search space is correct. This framework for training a sequential series of discriminative deep neural networks in a series of marginal spaces of increasing dimensionality can be referred to as Marginal Space Deep Learning (MSDL). In MSDL, deep learning is utilized to automatically learn high-level domain-specific image features directly from the medical image data. A feed-forward neural network is a neural network structure with an efficient training algorithm called back-propagation. Although powerful enough to approximate complicated target functions, a large feed-forward neural network tends to over-fit the training data. It is difficult to train a network with more than two hidden layers with good generalization capability. In a possible embodiment, unsupervised pre-training followed by supervised fine-tuning can be used to overcome the over-fitting issue. This technique can be used to train networks with three or more hidden layers. The pre-training can be treated as an unsupervised learning process to discover powerful image features from the input image data. Various deep learning techniques, such as an auto-encoder (AE) or a restricted Boltzman machine (RBM), can be used to pre-train a hidden layer. FIG. 2 illustrates an exemplary AE neural network. As shown in FIG. 2, the AE 200 is a feed-forward neural network with one hidden layer 204. The AE 200 has an input layer $L_1$ 202, the hidden layer $L_2$, and an output layer $L_3$ 206. If the AE 200 is a fully connected network, each node in the input layer 202 can correspond to a respective voxel or pixel of an image patch. Ignoring the bias term (the nodes labeled as +1 in FIG. 2), the input and output layers 202 and 206, respectively have the same number of nodes. The goal of an AE is to minimize the difference between the input and output vectors. If the hidden layer 204 has a size equal to or larger than the input layer 202, an AE may learn an identify transformation. To prevent such a trivial solution, an AE can be set up with a hidden layer 204 with fewer nodes than the input layer 202. The nodes of the hidden layer 204 can be calculated as a function of a bias term and a weighted sum of the nodes of the input layer 202, where a respective weight is assigned to each connection between a node of the input layer 202 and a node in the hidden layer 204. The bias term and the weights between the input layer 202 and the hidden layer 204 are learned in the training of the AE 200, for example using a back-propagation algorithm.

A denoising auto-encoder (DAE) may be used to learn a more meaningful representation of the input image data. In a DAE, a certain percentage (e.g., 50%) of the input nodes are randomly selected to be disturbed (e.g., set the value equal to zero) and the DAE is required to reconstruct the original input vector given a contaminated observation. The hidden layer in a DAE may have more nodes than the input layer to achieve an over-complete representation. According to an advantageous embodiment, in order to train the discriminative deep neural network for a particular marginal search space (step 108 of FIG. 1), after training an AE (or DAE), the output layer is discarded and another AE (or DAE) is stacked using the activation response of the already trained hidden layer as input to the new AE (or DAE). This process can be repeated to train and expand a network layer by layer. In a possible implementation, after pre-training a number of hidden layers, the output of the hidden layers can be treated as high-level image features and used to train a discriminative classifier for detecting the anatomical object in the current parameter space. Alternatively, an additional layer for the target output can be added to the network and the whole network can be refined using back-propagation.

As described above, the method of FIG. 1 uses deep neural networks to train pose classifiers in a series of marginal search spaces for anatomical object detection in medical image data (step 108 of FIG. 1). According to an advantageous implementation, a stacked denoising auto-encoder (DAE) can be used to train one or more of the discriminative classifiers. However, the present invention is not limited to this particular type of deep neural network and other types of deep neural networks, such as a convolutional neural network (CNN), stacked RBM, or a sparse AE, can also be used to train a discriminative classifier.

In a second embodiment, the method of FIG. 1 can use deep neural networks to train a series of regressors, each of which calculates, for each hypothesis in the search space, a difference vector from that hypothesis to predicted pose parameters of the object in the search space. This framework for training a sequential series of deep neural network regressors in a series of marginal spaces of increasing dimensionality can be referred to as Marginal Space Deep Regression (MSDR). In MSDR, a mapping function is learned from the current hypothesis parameters to the correct object parameters in each marginal search space. The mapping function has as input, an image patch corresponding to the current hypothesis parameters and as output the target parameter displacement. Each current hypothesis will yield a new hypothesis through the regression function which converges to the correct object parameters when learned successfully. The regressed hypotheses are passed through the incrementally increasing marginal spaces during both the training and objected detection in a new image. Possible advantages of MSDR relative to traditional discriminative learning are that MSDR heavily leverages context information, MSDR learns a smoother output function than a binary classifier which improves robustness, and MSDR is efficient by learning only in the projected subspaces (marginal search spaces). In addition, a regression function trained using a deep neural network can be iteratively applied to converge to the correct parameter region and eliminate outliers.

In MSDR, for a particular search space, the complex problem of learning a regression function from image data is solved by using a deep learning artificial neural network architecture that extracts directly from an image patch, the relevant features. According to an advantageous implementation, complex image patterns can be encoded in hierarchical features by learning one or more hidden layers by stacking deep neural network architectures, as described above. To solve the regression problem for a particular search space, at the output layer either a discretized multi-class classifier or a linear/non-linear regressor can be trained on top of the neural network features extracted by the learned hidden layers. Accordingly, such a deep neural network regression function has the ability to encode complex patterns hierarchically with no dependency on hand-crafted image features, and the ability to take advantage of unlabeled data to pre-train the underlying neural network (e.g., using stacked auto-encoder architectures or a deep-belief network). Such a trained deep neural network regressor also has the ability to solve multi-class problems. Object detection can be realized, for example, by hierarchical regression searches in an input image over the learned parameters spaces and taking the top hypotheses in the final parameter space. Object tracking can be accomplished similarly starting from the parameter set given by the object in a reference image.

Figure 3:
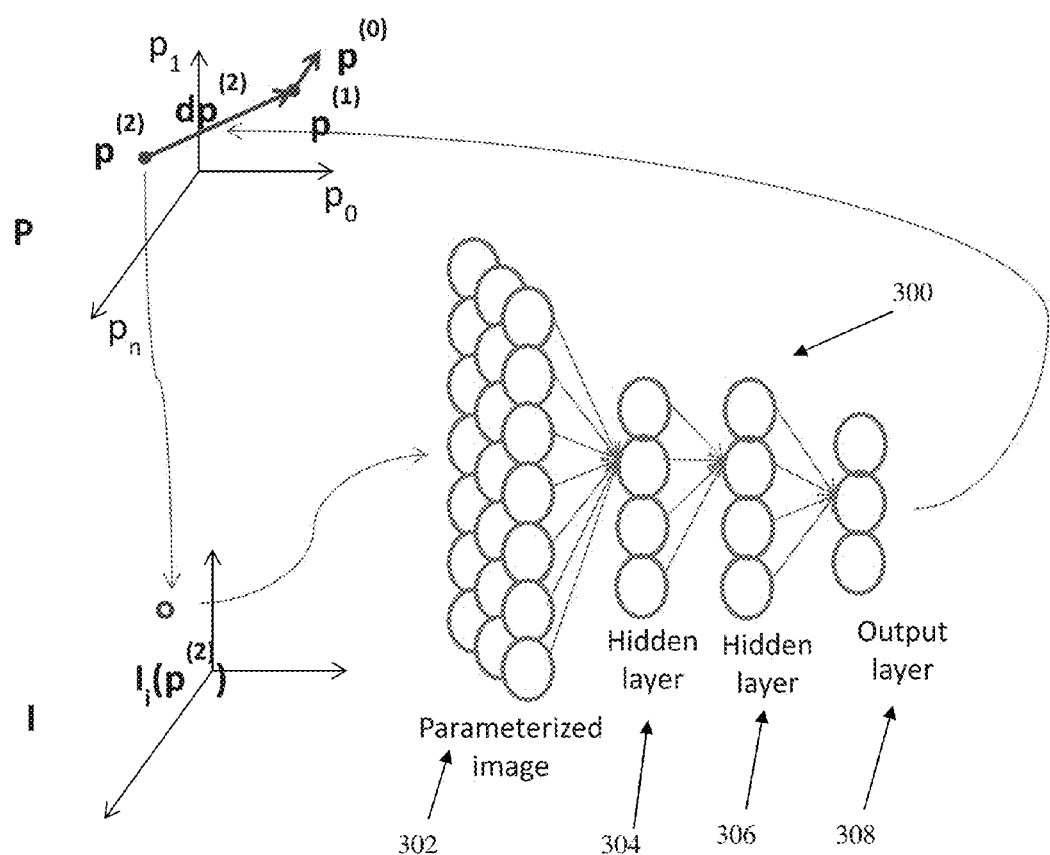
FIG. 3 illustrates training a deep multi-layer neural network regressor for a particular parameter space.

In order to train a deep neural network regressor (step 108 of FIG. 1), given a database of training images with the target object annotated in all or a subset of the training images, the object location (pose) is parameterized and the marginal spaces hierarchy is established, as described above in step 104. As described above in step 106, hypotheses are generated in the current search space. For the first search space, the hypotheses are generated directly from the current range, and for the other search spaces, the hypotheses are generated from the current hypotheses set augments with additional parameters which are sampled from the current corresponding range. Given the set of hypotheses for the current search space, a deep multi-layer neural network is trained having as input the sub-image (image patch) parameterized by the corresponding hypothesis parameters and as output the difference between the current parameters and the target or ground truth parameters of the target anatomical object for the current search space. FIG. 3 illustrates training a deep multi-layer neural network regressor for a particular parameter space. As shown in FIG. 3, P is the current parameter space (marginal space), $p^{(2)}$ is the parameters of a hypothesis in the parameter space, from which an image patch $I_i(p^{(2)})$ is generated from the $i^{th}$ image in the image space I. The parameterized image patch is used as input to a multi-layer deep neural network 300 and the supervised output is given by the parameter difference $dp^{(2)}$ between the hypothesis parameters $p^{(2)}$ and the ground truth parameters $p^{(1)}$ in the current parameter space P and optionally a confidence measure. The deep neural network 300 can be trained directly on the difference to the ground truth (in which case $p^{(1)}$ is the annotated parameter set) or the deep neural network 300 can be trained on a displacement towards ground truth in the training image. The deep neural network 300 has an input layer 302, multiple hidden layers 304 and 306, and an output layer 308. The input layer 302 directly inputs image patches corresponding to the parameters of hypotheses for the current parameter space. The hidden layers 304 and 306 can be trained to hierarchically extract features from the input image patches by stacking multiple deep neural network architectures in an unsupervised pre-training phase. The output layer 308 calculates displacement vector between the hypothesis parameters for each input image patch and the parameters of the target anatomical object for the current parameter space. An inverse of the distance of the estimated image patch to the ground truth image patch for the anatomical object location is used to train the confidence score.

For the deep neural network architecture and training, various types of neural networks can be used, such as convolutional neural networks (CNN), stacked restricted Boltzmann machine (RBM), or stacked auto-encoders (AE). In the case of RBM or AE, we can pre-train the networks in an unsupervised manner using all of the available training images (including non-annotated training images) to determine the representative features that characterize the class of data from a large database, prior to supervised training using the subset of annotated training images. In an advantageous embodiment, the deep neural network is trained using a stacked denoising auto-encoder (DAE) in two stages. The first stage is unsupervised where each layer of the multi-layer deep neural network is trained to reconstruct the input. In this stage, a virtual layer similar to the input is added to the output and the error to the input is minimized in this virtual layer to learn the weights for the nodes of each hidden layer. The second stage is supervised and the whole network error is minimized relative to the output training data starting from the pre-trained network weights. One characteristic of the DAE is that it randomly drops a certain percentage (up to 50%) of the inputs during training, which significantly increases the robustness of the resulting classifier or regressor. The output parameter space can be either directly regressed using a linear function or it can be discretized relative to the parameter range and solved as a multi-class classification problem. The second formulation has an advantage that it can directly encode the output probability and can generate multiple hypotheses, for example for different anatomical objects.

The set of current hypotheses for the current parameter space are then propagated through the trained deep neural network, and in a possible embodiment, the new set of hypotheses can be iteratively refined using the same deep neural network or through a newly trained deep neural network. This iterative process can eliminate samples far from the solution (non-overlapping) and generate samples closer to the true position to improve precision. FIG. 3 shows the results of this iterative process. As shown in FIG. 3, the image patch $I_t(p^{(2)})$ for the current hypothesis parameters $p^{(2)}$ is input to the deep neural network 300 in a first iteration, and the displacement vector $dp^{(2)}$ output by the deep neural network 300 maps the hypothesis parameters $p^{(2)}$ to the target parameters $p^{(1)}$. In a second iteration, the parameters $p^{(1)}$ are then input back into the deep neural network 300 in order to refine the estimated target parameters, and the deep neural network 330 outputs a displacement vector that maps the parameters $p^{(1)}$ to the refined target parameters $p^{(0)}$. Once the hypotheses for a particular marginal search space are run through the trained deep neural network, a new set of hypotheses is augmented with new parameters from the subsequent marginal space and the process is repeated for the subsequent marginal space. This results in a respective trained deep neural network regressor for each of the marginal spaces.

Figure 4:
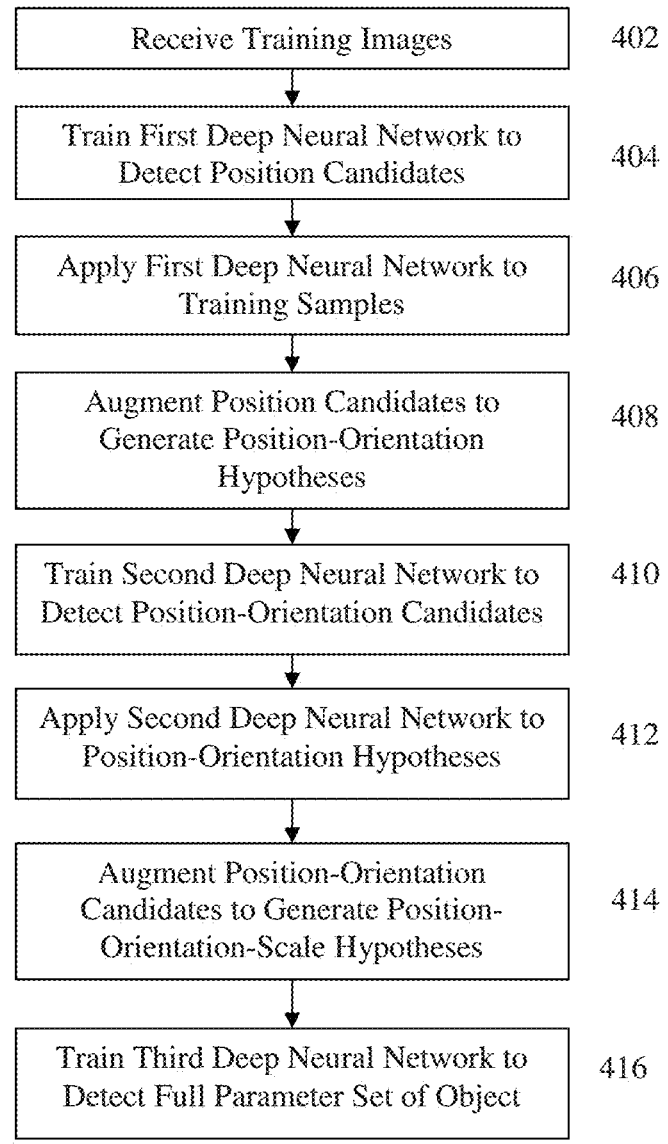
FIG. 4 illustrates training a series of deep neural networks in a series of marginal search spaces with increasing dimensionality according to an embodiment of the present invention.

FIG. 4 illustrates training a series of deep neural networks in a series of marginal search spaces with increasing dimensionality according to an embodiment of the present invention. In particular, the method of FIG. 4 provides a detailed method for training a series of deep neural networks for anatomical object detection in medical images when the parameter space of an anatomical object in a medical image is divided into marginal search spaces of position, position-orientation, and position-orientation-scale. Referring to FIG. 4, at step 402, training images are received. Step 402 of FIG. 4 can be implemented similarly to step 102 of FIG. 1. The training images can be 2D or 3D images, depending on the imaging modality and anatomical object to be detected. The description of FIG. 4 assumes that the images are 3D images and refers to the elements of the images as voxels. It is to be understood that the method of FIG. 4 can be similarly applied to 2D images and the term "pixel" can be substituted for "voxel" throughout the description of FIG. 4.

At step 404, a first deep neural network is trained to detect position candidates based on the training images. In a possible implementation, the first deep neural network may be a discriminative deep neural network that inputs voxels of an image as hypotheses and for each voxel calculates a probability that an image patch centered at the voxel is the object of interest. In this case, ground truth positions of anatomical objects in the training images can be used as positive training samples and randomly selected positions farther than a predetermined distance from the ground truth positions in the training images can be used as negative training samples. In another possible implementation, the first deep neural network may train a regressive function that inputs voxels of an image as hypotheses and calculates a difference vector for each input resulting in a predicted position calculated for each input voxel. In this case, a number of position hypotheses can be selected randomly from each training image, with the ground truth displacement to the position of the target anatomical object in the training image known for each position hypothesis. As described above, the first deep neural network (either discriminative or regressor) can be trained in two stages of unsupervised pre-training of the hidden layers (e.g., using stacked DAE) for learning complex features from input image patches and supervised training of the output layer based on the features extracted by the hidden layers and the annotated training samples.

At step 406, training samples are passed through the trained first deep neural network and a number of best position candidates are kept. For the discriminative deep neural network, a number of position hypotheses having the highest probability as calculated by the trained first deep neural network can be kept as the position candidates for each training image. For the deep neural network regressor, a confidence score can be calculated for each difference vector or each predicted position calculated by the trained first deep neural network, and a number of predicted positions with the highest confidence scores are kept as the position candidates At step 408, the position candidates are augmented with orientation parameters to generate hypotheses in the position-orientation search space. For example, a plurality of position-orientation hypotheses can be generated for each position candidate by rotating each image patch centered at a position candidate to a plurality of possible rotations. The range of these rotations can be determined by the range of orientations of the ground truth objects in the annotated training data.

At step 410, a second deep neural network is trained to detect position-orientation candidates based on the position-orientation hypotheses. In a possible implementation, the second deep neural network may be a discriminative deep neural network that inputs image patches of an image corresponding to the hypotheses in the position-orientation search space and for each image patch calculates a probability that the image patch is the object of interest. In another possible implementation, the second deep neural network may train a regressive function that inputs image patches of an image corresponding to the hypotheses in the position-orientation search space and calculates a difference vector in the position-orientation parameter space for each input resulting in a predicted position and orientation and a corresponding image patch in the image. The second deep neural network (either discriminative or regressor) can be trained in two stages of unsupervised pre-training of the hidden layers (e.g., using stacked DAE) for learning complex features from input image patches corresponding to the position-orientation hypotheses and supervised training of the output layer based on the features extracted by the hidden layers and the position-orientation hypotheses. Accordingly, the second deep neural network is trained based only on the position-orientation hypotheses that are generated from the position candidates detected using the first trained deep neural network.

At step 412, the position-orientation hypotheses are passed through the trained second deep neural network and a number of best position-orientation candidates are kept. For the discriminative deep neural network, a number of position-orientation hypotheses having the highest probability as calculated by the trained second deep neural network can be kept as the position-orientation candidates for each training image. For the deep neural network regressor, a number of image patches corresponding to the predicted positions and orientations with the highest confidence scores are kept as the position-orientation candidates.

At step 414, the position-orientation candidates are augmented with scale parameters to generate hypotheses in the position-orientation-scale search space. For example, a plurality of position-orientation-scale hypotheses can be generated for each position-orientation candidate by scaling each image patch corresponding to a position-orientation candidate to a plurality of possible scales. The range of these scales can be determined by the range of scales of the ground truth objects in the annotated training data.

At step 416, a third deep neural network is trained to detect a full parameter set (position-orientation-scale) of the object of interest based on the position-orientation-scale hypotheses. In a possible implementation, the third deep neural network may be a discriminative deep neural network that inputs image patches of an image corresponding to the hypotheses in the position-orientation-scale search space and for each image patch calculates a probability that the image patch is the object of interest. In another possible implementation, the third deep neural network may train a regressive function that inputs image patches of an image corresponding to the hypotheses in the position-orientation-scale search space and calculates a difference vector in the position-orientation-scale parameter space for each input resulting in a predicted position, orientation, and scale and a corresponding image patch in the image. The third deep neural network (either discriminative or regressor) can be trained in two stages of unsupervised pre-training of the hidden layers (e.g., using stacked DAE) for learning complex features from input image patches corresponding to the position-orientation-scale hypotheses and supervised training of the output layer based on the features extracted by the hidden layers and the position-orientation-scale hypotheses. Accordingly, the third deep neural network is trained based only on the position-orientation-scale hypotheses that are generated from the position-orientation candidates detected using the second trained deep neural network.

Figure 5:
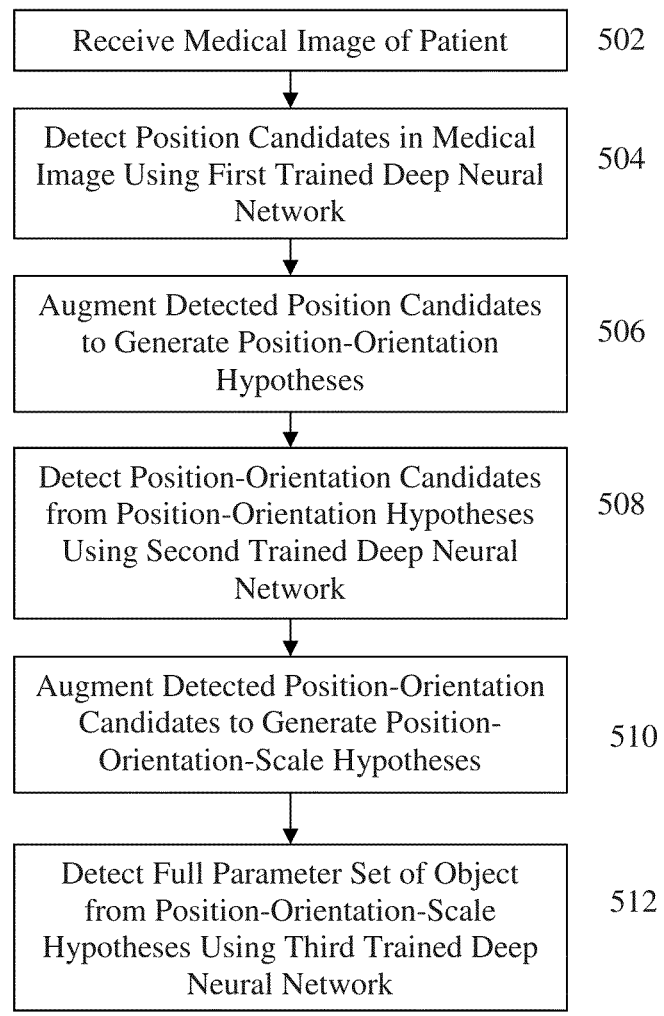
FIG. 5 illustrates a method of detecting an anatomical object in a medical image using a series of trained deep neural networks according to an embodiment of the present invention.

FIG. 5 illustrates a method of detecting an anatomical object in a medical image using a series of trained deep neural networks according to an embodiment of the present invention. The method of FIG. 5 can be performed using a series of deep neural networks trained using the method of FIG. 4. Referring to FIG. 5, at step 502, a medical image of the patient is received. The medical image can be 2D or 3D and can be acquired using any type of medical imaging modality, such as but not limited to CT, MRI, ultrasound, X-ray fluoroscopy, DynaCT, etc. The medical image can be received directly from an image acquisition device, such as a CT scanner, MRI scanner, etc., or can be received by loading a previously acquired medical image of the patient from a memory or storage of a computer system. The description of FIG. 5 assumes that the medical image is a 3D image and refers to the elements of the medical image as voxels. It is to be understood that the method of FIG. 5 can be similarly applied to 2D images and the term "pixel" can be substituted for "voxel" throughout the description of FIG. 5.

At step 504, position candidates are detected in the medical image using a first trained deep neural network. The first deep neural network operates directly on the voxels of the medical image, and not on handcrafted features extracted from the medical image. The first deep neural network inputs image patches centered at voxels of the medical image and calculates a number of position candidates in the medical image based on the input image patches. The first deep neural network can evaluate every voxel in the medical image or a subset of voxels in the medical image to calculate the position candidates. In a possible implementation, the first trained deep neural network may be a discriminative deep neural network that inputs image patches centered at voxels of the medical image and for each voxel calculates a probability that the voxel is the center position of the target anatomical object. In this case, a number of position candidates with highest probabilities calculated by the first trained deep neural network are kept. In another possible implementation, the first deep neural network may train a regressive function that inputs image patches centered at voxels of the medical image and calculates a difference vector for each voxel resulting in a predicted center position of the anatomical object calculated for each input voxel. In this case, the first trained deep neural network can also calculate a confidence score for each predicted position and a number of predicted positions with the highest confidence scores are kept.

At step 506, the position candidates detected by the first trained deep neural network are augmented with orientation parameters to generate position-orientation hypotheses. For example, a plurality of position-orientation hypotheses can be generated for each detected position candidate by rotating each image patch centered at a position candidate to a plurality of possible orientations sampled from a predetermined range of orientations for the target anatomical object. The predetermined range of orientations can be determined by the range of orientations of the ground truth objects in a set of annotated training data. It should be noted that in the case in which the second trained deep neural network used to detect position-orientation candidates in step 508 is a trained deep neural network regressor, the augmenting of the position candidates with orientation parameters may not be performed in some implementations. Although the additional position-orientation hypotheses may lead to increased accuracy of the position-orientation estimation, since the trained deep neural network regressor will predict the position and orientation of the target anatomical object and a corresponding target image patch for each input image patch corresponding to a position candidate, the trained deep neural network regressor can be run directly on image patches corresponding to the position candidates and it is not necessary to augment the position candidates with multiple orientation parameters.

At step 508, position-orientation candidates are detected from the position-orientation hypotheses using a second trained deep neural network. The second deep neural network operates directly on the image patches of the medical image corresponding to the position-orientation hypotheses. The second deep neural network inputs the image patches corresponding to the position-orientation hypotheses and calculates a number of position-orientation candidates in the medical image based on the input image patches. In a possible implementation, the second trained deep neural network may be a discriminative deep neural network that inputs the image patches corresponding to the position-orientation hypotheses and for each position-orientation hypothesis calculates a probability that the corresponding image patch is target anatomical object. In this case, a number of position-orientation candidates with highest probabilities calculated by the second trained deep neural network are kept. In another possible implementation, the second deep neural network may train a regressive function that inputs the image patches corresponding to the position-orientation candidates and calculates a difference vector for each image patch resulting in a predicted position and orientation of the anatomical object and corresponding predicted image patch calculated for each input position-orientation hypothesis. In this case, the second trained deep neural network can also calculate a confidence score for each predicted image patch and a number of predicted image patches with the highest confidence scores are kept as the position-orientation candidates.

At step 510, the position-orientation candidates detected by the second trained deep neural network are augmented with scale parameters to generate position-orientation-scale hypotheses. For example, a plurality of position-orientation-scale hypotheses can be generated for each detected position-orientation candidate by scaling each image patch corresponding to a position-orientation candidate to a plurality of possible scales sampled from a predetermined range of scales for the target anatomical object. The predetermined range of scales can be determined by the range of scales of the ground truth objects in a set of annotated training data. It should be noted that in the case in which the third trained deep neural network used to detect the full parameter set of the target anatomical object in step 508 is a trained deep neural network regressor, the augmenting of the position-orientation candidates with scale parameters may not be performed in some implementations. Although the additional position-orientation-scale hypotheses may lead to increased accuracy of the full parameter set estimation, since the trained deep neural network regressor will predict the position, orientation, and scale of the target anatomical object and a corresponding target image patch for each input image patch corresponding to a position-orientation candidate, the trained deep neural network regressor can be run directly on image patches corresponding to the position-orientation candidates and it is not necessary to augment the position-orientation candidates with multiple scale parameters.

At step 512, the full parameter set (position, orientation, and scale) of the target anatomical object is detected from the position-orientation-scale hypotheses using a third trained deep neural network. The third deep neural network operates directly on the image patches of the medical image corresponding to the position-orientation-scale hypotheses. The third deep neural network inputs the image patches corresponding to the position-orientation-scale hypotheses and calculates the full parameter set defining the pose of the anatomical object in the medical image based on the input image patches. In a possible implementation, the third trained deep neural network may be a discriminative deep neural network that inputs the image patches corresponding to the position-orientation-scale hypotheses and for each position-orientation-scale hypothesis calculates a probability that the corresponding image patch is the target anatomical object. In this case, the image patch corresponding to the position-orientation-scale hypothesis with the highest probability calculated by the third trained deep neural network can be output as the detection result for the anatomical object. It is also possible that a number of image patches corresponding to position-orientation-scale with the highest probabilities can be clustered to generate the final detection result for the anatomical object. In another possible implementation, the third deep neural network may train a regressive function that inputs the image patches corresponding to the position-orientation-scale hypotheses and calculates a difference vector for each image patch resulting in a predicted position, orientation, and scale of the anatomical object and corresponding predicted image patch calculated for each input position-orientation-scale hypothesis. In this case, the third trained deep neural network can also calculate a confidence score for each predicted image patch, and the image patch with the highest confidence score can then be output as the detection result for the anatomical object. It is also possible that a number of predicted image patches with the highest confidence scores can be clustered to generate the final detection result for the anatomical object.

The detected anatomical object can be displayed on a display device of a computer, for example, by displaying the medical image and indicating the pose of the target anatomical object on the medical image using a bounding box with the detected position, orientation, and scale. According to an advantageous embodiment, the method of FIG. 5 can be extended to segmentation of the of the target anatomical object. For example, a mean model (e.g., 3D mesh) of the target anatomical object can be calculated from a set of annotated training data, and once the full parameter (position, orientation, and scale) of the target anatomical object is detected in the medical image, the mean model can be rigidly registered to the medical image using the detected position, orientation, and scale of the target anatomical object, resulting in a segmented model of the target anatomical object in the medical image. In this case, local boundary refinement can be performed after the mean model is registered to the medical image. In the local boundary refinement, each boundary point of the segmented model of the target anatomical object is refined by evaluating points in both directions along a line normal to the model surface using the a trained boundary detector. The refined model can then be projected to a learned shape space of the target anatomical object using an active shape model. The steps of refining the model using the trained boundary detector and projecting the refined model to the learned shape space can be iterated until convergence or for a predetermined number of iterations. In a possible implementation, the trained boundary detector can be a deep neural network that is directly applied to the image data. Alternatively, the trained boundary detector can be use handcrafted features, such as steerable features, extracted from the image data.

The methods of FIGS. 4 and 5 describe training a series of deep neural networks and anatomical object detection using a trained series of deep neural networks for an embodiment in which the parameter space for the pose of an anatomical object is divided into the marginal search spaces of position, position-orientation, and position-orientation-scale. However, the present invention is not limited to these particular marginal shape spaces. For example, the methods can be similarly performed using marginal shape spaces of position, position-scale, and position-scale-orientation. It is to be understood, that embodiments of the present invention can be applied to any series of marginal search spaces with increasing dimensionality.

The methods of FIGS. 1 and 4 train a deep neural network for each of the marginal shape spaces. In one possible implementation, each of the trained deep neural networks is a discriminative deep neural network. In another possible implementation, each of the trained deep neural networks is a deep neural network regressor. Other hybrid implementations are also possible, where discriminative deep neural networks and deep neural network regressors are used for different ones of the marginal search spaces or where a deep neural network (discriminative or regressor) is used for one or more of the marginal search spaces and another type of classifier is trained for one or more of the marginal search spaces.

Figure 6:
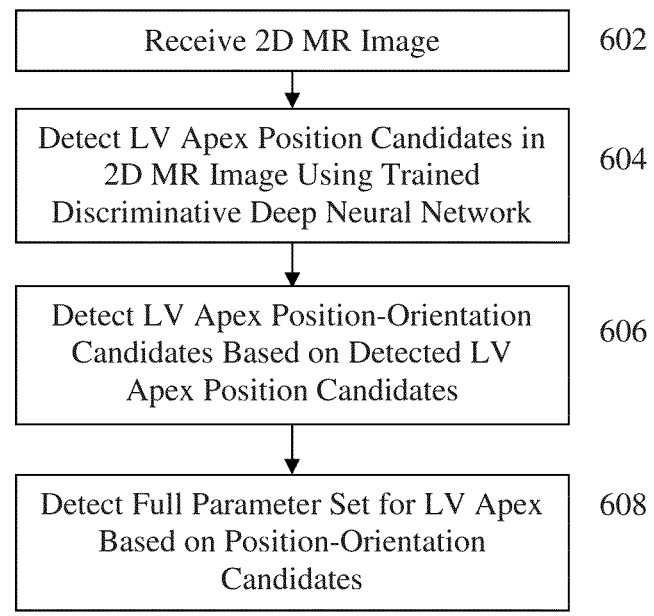
FIG. 6 illustrates a method for detecting a left ventricle apex in a 2D MR image using marginal space deep learning according to an embodiment of the present invention.

FIG. 6 illustrates a method for detecting a left ventricle apex in a 2D MR image using marginal space deep learning according to an embodiment of the present invention. The method of FIG. 6 provides an example in which deep neural networks are applied to detect the left ventricle (LV) apex in a 2D MR image. According to various possible implementations, the method of FIG. 6 can be implemented using discriminative deep neural networks for each marginal search space, using both a discriminative deep neural network and deep neural network regressors, or using a discriminative deep neural network with other types of classifiers. Although the method of FIG. 6 is described as detecting the LV apex in a 2D MR image, it is to be understood that variations of the method can be similarly applied to other anatomical objects and other 2D or 3D imaging modalities. Referring to FIG. 6, at step 602, a 2D MR image is received. The 2D MR image can be an MR image of a heart region of a patient. The 2D MR image can be received directly from an MR scanner or can be received by loading a previously acquired 2D MR image of a patient.

At step 604, LV apex position candidates are detected in the 2D MR image using a trained discriminative deep neural network. The trained discriminative deep neural network is trained based on training images in which the LV apex is annotated. For each training image, an image patch (e.g., 32×32 pixels) centered at the annotated LV apex can be taken as a positive training sample, and another image patch of the same size located more than a predetermined distance (e.g., 5 mm) away from the annotated LV apex can be randomly selected as a negative training sample. As described above, the discriminative deep neural network can be trained using an unsupervised pre-training stage in which the hidden layers are trained (e.g., using stacked DAE) to learn complex features from input image patches, followed by supervised training of the output layer based on the features extracted by the hidden layers and the annotated training samples to calculate a probability for each input image patch and classify an input image patch as positive or negative based on the probability.

In an exemplary test performed by the present inventors a training set of 7961 2D MR images from 184 patients was used. 75% of the training images were randomly selected for training (5970 images from 139 patients) and 25% for testing (1991 images from 46 patients). In this experiment, images from the same patient appear in either the training set or the testing set, but not both (patient-wise cross validation). For each training image, an image patch of 32×32 pixels centered at the annotated LV apex was selected as a positive training sample, and another image patch of the same size located more than 5 mm away from the annotated LV apex was be randomly selected as a negative training sample. With a balanced positive/negative training samples, a traditional MSL position classifier trained based on Haar wavelet features extracted from the training images using a probabilistic boosting tree (PBT) achieved a test error of 30% for LV apex position detection. The MSL position classifier can be trained on a very large number of negative samples. When the MSL position classifier was trained on 10 million negative training samples randomly selected from the training set, the test error of the MSL position classifier was reduced to 23%. A support vector machine (SVM) trained on the original input patch (using raw image intensity as features with 32×32=1024 features) achieved a test error of 13%. CNN achieved an error of 16.9%. A stacked DAE (SDAE) with layers having sizes of 1024-1024-300-100-2 trained based on the training samples achieved a test error of 7.3%, which is significantly better than the other classification schemes.

Figure 7:
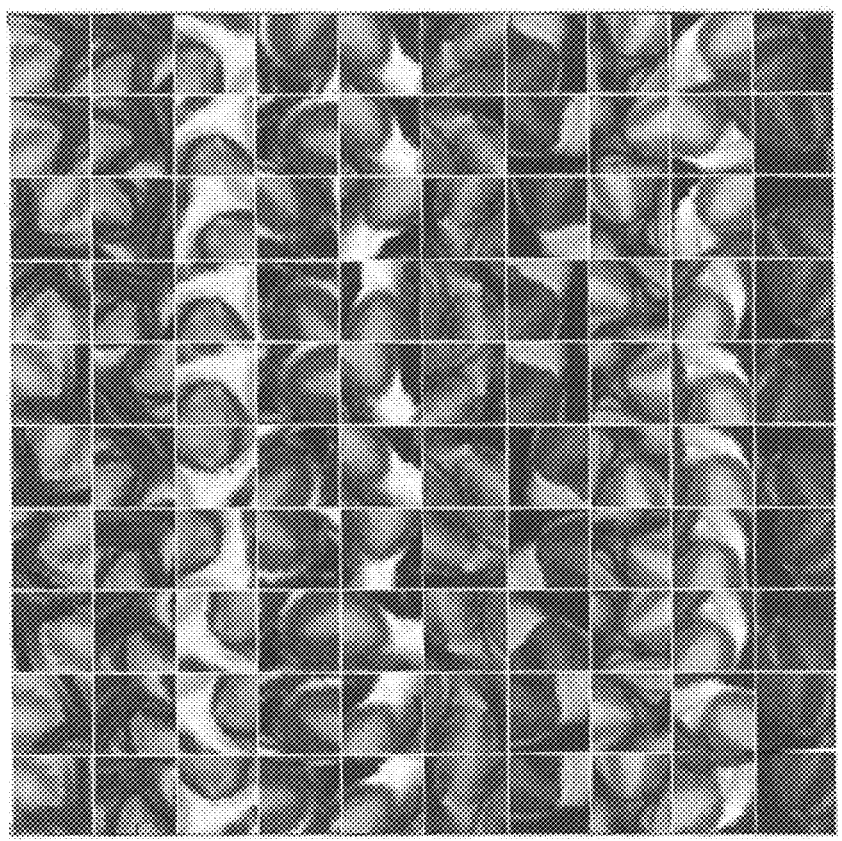
FIG. 7 illustrates exemplary enriched positive training samples with random rotations for LV apex position detection.
Figure 8:
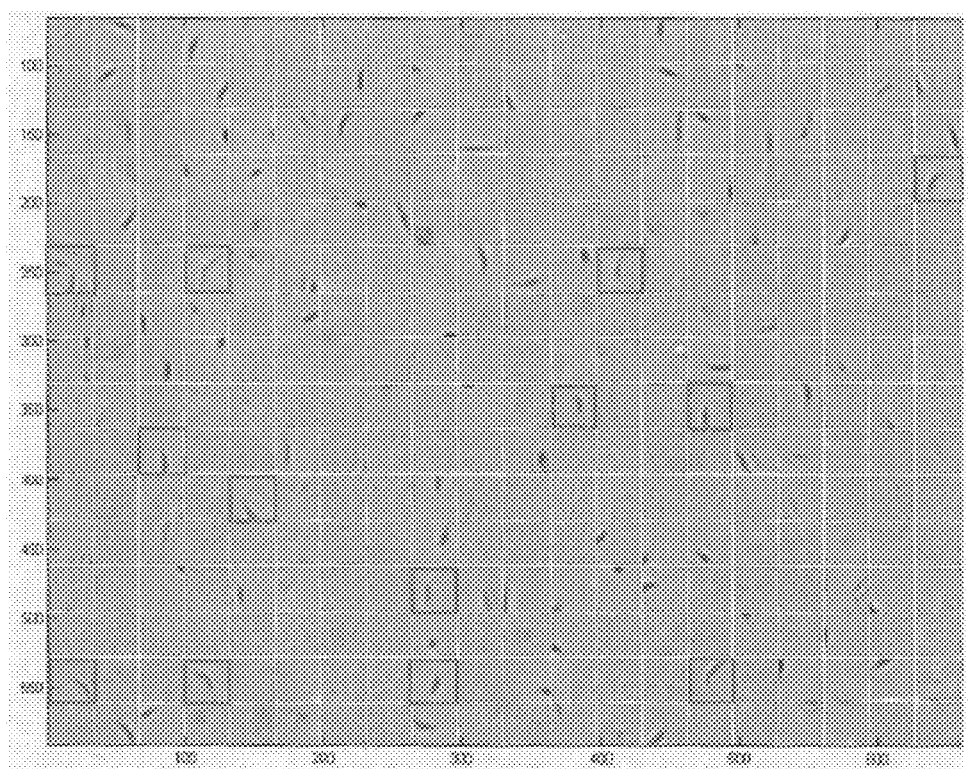
FIG. 8 illustrates exemplary learned weights of a first hidden layer of stacked denoising auto-encoder (DAE)

A major challenge with detection of the LV apex position in 2D MR images is that there is a large variation of the LV orientation, which leads to a large variation of the appearance of the LV apex based on the orientation of the MR image. According to an advantageous implementation, additional positive training samples for the LV apex detection can be generated by rotating each image patch centered at a ground truth LV apex position to a plurality of possible rotations. For example, for each training image, in addition to the original image patch centered at the annotated LV apex position, nine randomly rotated image patches centered at the annotated LV apex position can be used as positive training samples. FIG. 7 illustrates exemplary enriched positive training samples with random rotations for LV apex position detection. As shown in FIG. 7, each column shows 10 positive training samples taken from one training image. The top image patch in each column is the original image patch centered at the LV apex position for the training image, and the other image patches in each column are the randomly rotated image patches. The negative training samples are not rotated. However, since more positive training samples are selected from each training image, ten negative training samples can be randomly sampled from each training image in order to balance the number of positive and negative training samples. By training the SDAE for detecting the LV apex position using the enriched training samples in the experiment performed by the present inventors, the test error was reduced from 7.3% to 3.1%. As described above, the trained hidden layers of the deep neural network learn high-level image features directly from the input image patches. FIG. 8 illustrates exemplary learned weights of a first hidden layer of stacked denoising auto-encoder (DAE). The learned weights shown in FIG. 8 can be treated as filters for extracting high-level image features. Some of the filters (learned weights) shown in FIG. 8 are similar to Gabor features, while some of the filters (highlighted with boxes in FIG. 8) are specific detectors of the LV apex with different orientations.

Once the discriminative deep neural network position detector is trained, the trained discriminative deep neural network is used to test each pixel in the 2D medical image and a number (e.g., 200) of candidates with largest classification scores (highest probabilities) are preserved as position candidates. In a possible implementation, since the LV apex is an anatomical landmark, the method can end at this step and output a position detected by the trained discriminative deep neural network as the LV apex position. In this case, cluster analysis can be performed on the detected position candidates and the center of the largest cluster can be used as the final detection result for the LV apex. However, the position-orientation, and position-orientation scale detection can be used as bootstrapped classifiers to remove false positives in the position detection. In the testing performed by the present inventors, if a detected LV apex is more than 10 mm away from the ground truth, the detection is considered to fail. Using only the position detector trained with SDAE for LV apex detection achieved a failure rate of 16.3%. For comparison, using the whole MSL pipeline trained using handcrafted image features (Haar wavelets for position and steerable features for position-orientation and position-orientation-scale) and the PBT achieved a failure rate of 21.1%. Accordingly, the position detector trained with SDAE outperformed the entire MSL pipeline using handcrafted image features. In a possible hybrid approach, the position candidates for the LV apex can be detected using the SDAE, and the position candidates can be fed to the MSL position-orientation and position-orientation-scale classifiers trained using the handcrafted image features (steerable features) and the PBT. Using this hybrid approach, a detection failure of 11.7% was achieved, which is about half of the failure rate of the original MSL.

Returning to FIG. 6, at step 606, position-orientation candidates for the LV apex are detected based on the detected position candidates. In a first possible embodiment, the hybrid approach describe above can be used, in which the trained deep neural network replaces the position detector in the MSL pipeline and the detected position candidates are fed to the MSL position-orientation classifier trained using steerable features and a PBT. In other possible embodiments, deep neural network learning can be further applied to perform the position-orientation estimation.

In a second possible embodiment, similar to the method of FIG. 5 described above, rotated image patches centered at each of the position candidates can be cropped and input into a second trained discriminative deep neural network classifier which is trained as a binary classifier to distinguish an image patch corresponding to a correct hypothesis from an image patch corresponding to an incorrect hypothesis. A number of position-orientation candidates with the best classifications scores are preserved. This works well for 2D images since there is only one degree of freedom for 2D rotation, Furthermore, the 2D image can be pre-rotated to a number of possible orientations and the rotated image patches can be generated by cropping the image patches from the corresponding pre-rotated images. However, this may be impractical for 3D since there are three degrees of freedom for 3D rotation and rotating a 3D volume is time consuming.

In a third possible embodiment, steerable features can be used as image features to incorporate position and orientation hypotheses generated from the position candidates. The steerable features are efficient under any position, orientation and scale. In this embodiment, instead of using a PBT to train a classifier, a deep neural network can be used to train a discriminative classifier for detecting position-orientation candidates instead of the classifier based on the steerable features, and instead of training the classifier directly on the input image patches. The trained discriminative classifier is then used to detect the position-orientation candidates based on steerable features of position-orientation hypotheses generated from the detected position candidates.

In a fourth possible embodiment, the position-orientation problem is formulated as a regression problem and a trained deep neural network regressor is used to detect the position-orientation candidates based on the position candidates detected by the trained discriminative deep neural network. Given the input image patches corresponding to the position candidates, the trained deep neural network regressor can directly calculate estimates of the position and orientation of the target object (e.g., LV apex). Furthermore, the trained deep neural network regressor can be augmented to output a confidence score for each estimated target image patch. To train this confidence score, an inverse of the distance of the estimated image patch to the ground truth apex position is used. For each preserved position candidate, a corresponding image patch centered at the position candidate is input to the trained deep neural network regressor and a target image patch is predicted based on the input image patch. In this embodiment, the image patch corresponding to the position candidate does not need to be rotated. The trained deep neural network regressor provides not only an estimate of the target object position and orientation, but also a confidence score that quantifies how reliable the estimate is. The estimated position-orientation image patches are then ranked using the confidence score and a number of position-orientation candidates with the largest confidence scores are preserved.

At step 608, the full parameter set (position, orientation, and scale) is detected for the LV apex based on the position-orientation candidates. This step can be performed similarly to the position-orientation estimation step using one the embodiments described for that step. For example, in a first possible embodiment, the detected position-orientation candidates are fed to the MSL position-orientation-scale classifier trained using steerable features and a PBT. In a second possible embodiment, each of the image patches corresponding to the position-orientation candidates can be scaled to a plurality of scales and the scaled image patches can be evaluated by a trained discriminative deep neural network to detect the image patch with the highest classification score. In a third possible embodiment, a discriminative deep neural network trained using steerable features can be used to evaluate the position-orientation candidates at different scales. In a fourth possible embodiment, a trained deep neural network regressor can be used to estimate a target position-orientation-scale image patch for each of the position-orientation candidates, and the target image patch having the highest confidence score can be selected as the final detection result.

Figure 9:
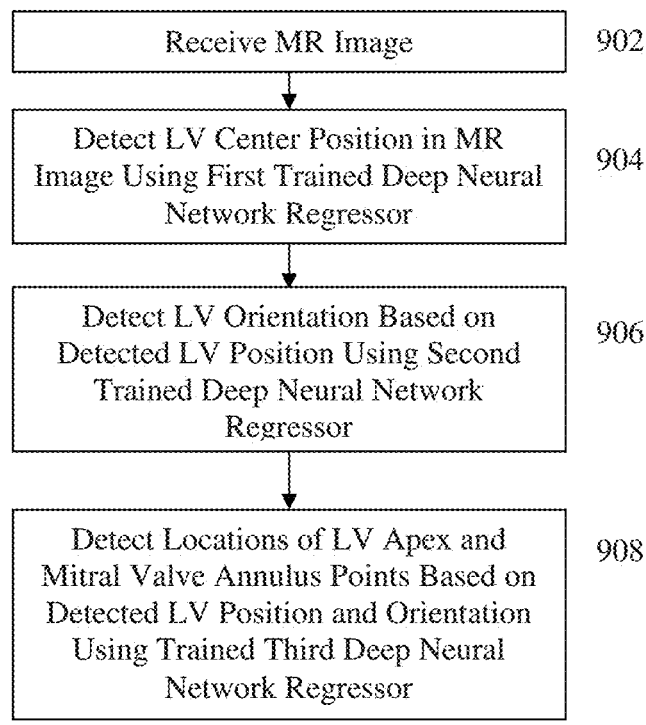
FIG. 9 illustrates a method for left ventricle (LV) landmark detection in MR cardiac long axis images using marginal space deep regression (MSDR) according to an embodiment of the present invention.
Figure 10:
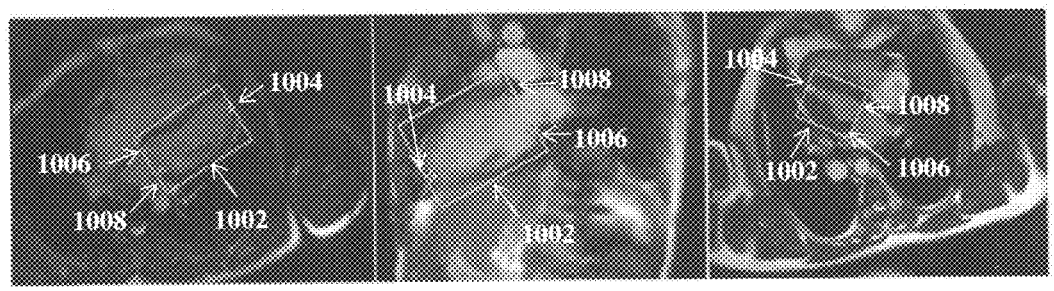
FIG. 10 illustrates exemplary LV landmarks in various MR cardiac long axis images.

FIG. 9 illustrates a method for left ventricle (LV) landmark detection in MR cardiac long axis images using marginal space deep regression (MSDR) according to an embodiment of the present invention. The method of FIG. 9 is an example in which a series of trained deep neural network regressors is used to detect multiple LV landmarks in a series of marginal spaces with increasing dimensionality. In particular, the method of FIG. 9 detects the locations of the LV apex and two mitral valve annulus points in MR cardiac long axis image. FIG. 10 illustrates exemplary LV landmarks in various MR cardiac long axis images. In particular, FIG. 10 shows an LV bounding box 1002 center at an LV center position, the LV apex 1004, and the mitral valve annulus points 1006 and 1008 in three MR long axis images. One difficulty with this detection problem is the large appearance and parameter variability characteristic to the MR images. All types of long axis views (e.g., 4-chamber view, 2-chamber view, and 3-chamber view) can be considered, which increases the difficulty of the problem.

Referring to FIG. 9, at step 902 an MR image is received. The MR image can be a 2D MR long axis image of any long axis view (e.g., 4-chamber view, 2-chamber view, or 3-chamber view). The MR image can be received directly from an MR scanner or received by loading a previously stored MR image from a memory or storage of a computer system. At step 904, an LV center position is detected in the MR image using a first trained deep neural network regressor. At step 906, an LV orientation is detected based on the detected LV position using a second trained deep neural network regressor. At step 908, locations of the LV apex and mitral valve annulus points are detected based on the detected LV position and orientation using a third trained deep neural network regressor. Instead of detecting a single anatomical object in a medical image in marginal search spaces of position, position-orientation, and position-orientation scale, the method of FIG. 9 performs the landmark detection in the following series of marginal search spaces:

LV position, LV position and orientation, and a full parameter set including the positions of the LV apex and mitral valve annulus points. That is, the method of FIG. 9 finds the position and orientation of the LV (in steps 904 and 906) and then uses this information to predict the locations of the LV apex and mitral valve annulus points (in step 908).

The first trained deep neural network regressor using for LV position detection in step 904 is trained on 2D displacements from image patches (e.g., 32×32 pixels) corresponding to training sample position hypotheses to an image patch centered at the ground truth LV center position in each training image. The second trained deep neural network regressor is trained using predicted image patches output by the first trained classifier rotated to a number of different orientations to predict an image patch centered at the LV center position with the correct LV orientation. The third trained deep neural network regressor is trained on 2D displacements corresponding to locations of each of the three LV landmarks (LV apex and mitral valve annulus points). The third trained deep neural network regressor inputs an image patch corresponding to a detected LV center location and LV orientation and outputs a first displacement vector that maps the input image patch to a location of the LV apex, a second displacement vector that maps the input image patch to a location of one of the mitral valve annulus points, and a third displacement vector that maps the input image patch to the other one of the mitral valve annulus points. In an exemplary implementation, a 3-level DAE with a discretized multi-class output for each parameter value can be trained for each marginal search space. The trained DAEs may limit the length of the displacement vector (e.g., up to 24 pixel displacements for translation) and the image can be scanned iteratively to determine the final parameter set for each marginal search space.

Figure 11:
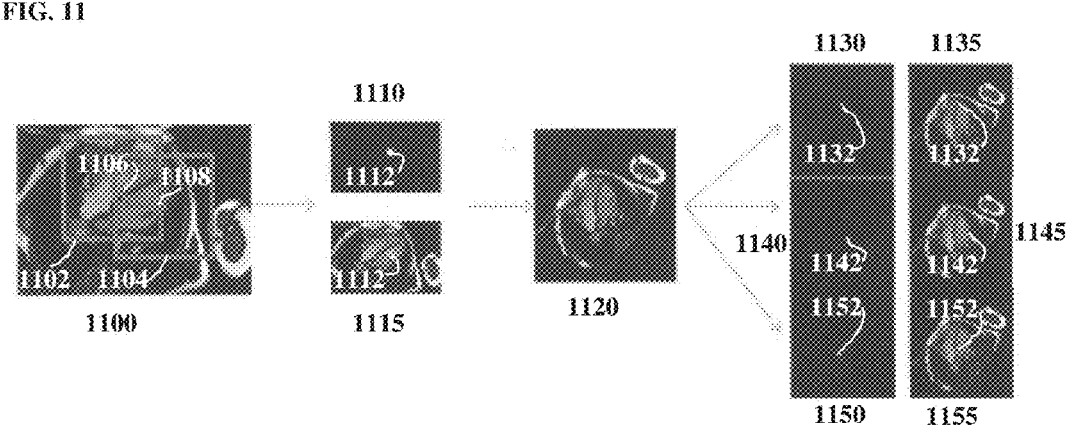
FIG. 11 illustrates exemplary results of detecting the LV landmarks in an MR image using the method of FIG. 9.

FIG. 11 illustrates exemplary results of detecting the LV landmarks in an MR image using the method of FIG. 9. As shown in FIG. 11, image 1100 shows a first detection stage (step 904 of FIG. 9), in which the LV position is detected using the first trained deep neural network regressor. As shown in image 1100, image patches 1102 and 1104 centered at various pixels in an MR image are input to the first trained deep neural network regressor, and the first trained deep neural network regressor calculates a respective displacement 1106 and 1108 for each image patch 1102 and 1104 from a center position of each image patch 1102 and 1104 to an LV center position. Image 1110 shows the detected LV center position 1112 detected by the first trained deep neural network regressor in the parameter space and image 1115 shows the detected LV center position 1112 in the MR image. As described herein, the first detection stage (step 904) detects a single LV center position. For example, the LV center position detected by the first trained deep neural network regressor with the highest confidence score can be propagated to the second detection stage (step 906). In an alternative implementation, multiple LV center position candidates can be propagated to the second detection stage. In the second detection stage (step 906), the LV orientation is detected based on the detected LV center position by the second trained deep neural network regressor. Image 1120 shows the MR image rotated to be aligned with the LV rotation detected by the second trained deep neural network regressor. As described herein, the first detection stage (step 904) predicts an image patch corresponding to a particular LV center position and LV orientation. In an alternative implementation, multiple LV position-orientation candidates can be propagated to the third detection stage. In the third detection stage (step 909), the positions of the LV apex and mitral valve annulus points are detected based on the detected LV center position and LV orientation by the third trained deep neural network regressor. Image 1130 shows the detected LV apex position 1132 detected by the third trained deep neural network regressor in the parameter space and image 1135 shows the detected LV apex position 1132 in the MR image. Image 1140 shows the detected position of the first mitral valve annulus point 1142 detected by the third trained deep neural network regressor in the parameter space and image 1145 shows the detected position of a first mitral valve annulus point 1142 in the MR image. Image 1150 shows the detected position of a second mitral valve annulus point 1152 detected by the third trained deep neural network regressor in the parameter space and image 1155 shows the detected position of the second mitral valve annulus point 1152 in the MR image.

Figure 12:
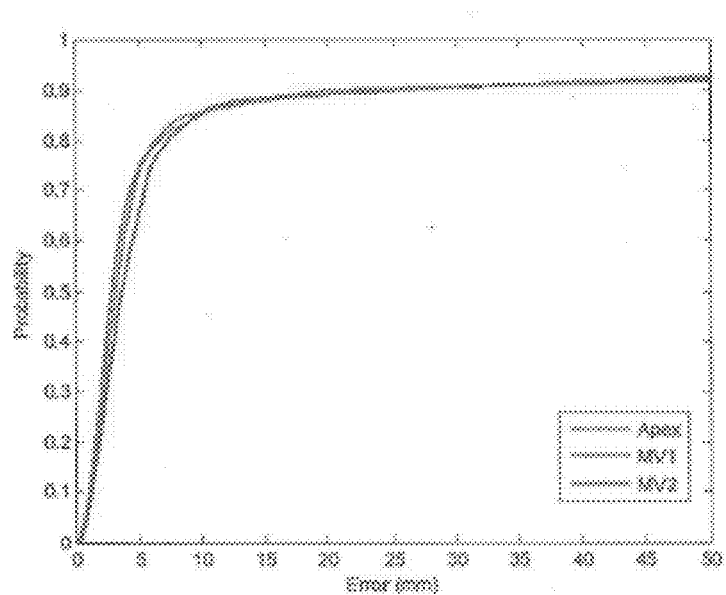
FIG. 12 illustrates the probability of detection errors on a testing set for the detection of LV apex and mitral valve annulus points.

The present inventors tested the method of FIG. 9 using a database of 7961 images from 184 patients, which was randomly split into 5970 images for training (75% of the data from 138 patients) and 1991 images for testing (25% of the data from 46 patients). The training and testing sets were disjoint at the patient level. For the first and second marginal search spaces, half of the original image was used with an image patch of 32×32 pixels. A 3-level DAE with discretized multi-class output for each parameter value was used for each marginal search space (up to 24 pixel displacements for translation). Each testing image was scanned iteratively to determine the final parameter set. FIG. 12 illustrates the probability of detection errors on the testing set for the detection of the LV apex and mitral valve annulus points. As shown in FIG. 12, 80% of the testing data has an error of less than 8 mm. Table 1 shows the performance of the method of FIG. 9 for detecting the LV center, LV apex, right mitral valve annulus point, and left mitral valve annulus point in the testing set without bootstrapping.

TABLE 1

| Anatomy | Mean | Median | $80^{th}$ percentile | Failure rate (>10 mm) |
|---|---|---|---|---|
| LV center | 9.09 | 4.80 | 8.44 | 5.00 |
| LV apex | 12.28 | 3.61 | 6.26 | 14.37 |
| MV right | 12.05 | 3.16 | 6.80 | 14.32 |
| MV left | 11.00 | 2.85 | 6.53 | 14.63 |

For comparison, detection of the LV apex using the traditional MSL framework achieves a mean error of 20.39 mm, a median error of 4.38 mm, 11.04 mm at 80%, and 21.1% outliers (error larger than 10 mm from ground truth). Performance of the LV landmark detection using MSDR can be further improved by bootstrapping the results through the newly trained multi-layer neural networks to filter the hypotheses set. The detection time for the testing using the MSDR framework of FIG. 9 was less than 2 seconds using a standard personal computer (PC).

When a deep neural network architecture is used for the underlying classifier for object detection in a particular parameter space, as in the embodiments described above, scalability may be limited when searching in high dimensional spaces (such as search over the 3D position in a volume) due to scanning with high dimensional and complex weight matrices learned for such deep neural networks. This may apply for convolutional layers as well as fully connected filters, even though the operations of convolutional layers can be performed efficiently, for example by mapping the convolution through Fourier space using a Fast Fourier transform (FFT). According to an embodiment of the present invention, a method for approximating the marginal space deep neural network architectures can be used to address such scalability challenges.

Figure 13:
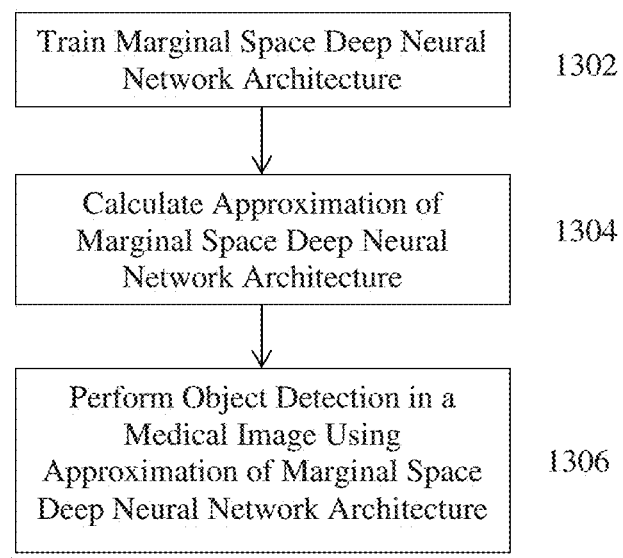
FIG. 13 illustrates a method of anatomical object detection by approximating a marginal space deep neural network architecture according to an embodiment of the present invention.

FIG. 13 illustrates a method of anatomical object detection by approximating a marginal space deep neural network architecture according to an embodiment of the present invention. The method of FIG. 13 can be applied to object detection using discriminative deep neural network architecture or a deep neural network regression function architecture. Referring to FIG. 13, at step 1302, a marginal space deep neural network architecture is trained for anatomical object detection. For example, the marginal space deep neural network architecture can be trained by training a series of deep neural networks for a series of marginal search spaces of increasing dimensionality using the method of FIG. 1 or the method of FIG. 4, described above. As described above, each deep neural network is trained by learning weights connecting nodes of multiple layers of the deep neural network. At step 1304, an approximation of the marginal space deep neural network architecture is calculated. The approximation of the marginal space deep neural network architecture is calculated by calculating a respective approximation of each trained deep neural network. The approximation of each trained deep neural network is calculated by approximating the learned weights of that trained deep neural network. At step 1306, the object detection in a medical image is performed using the approximation of the marginal space deep neural network architecture instead of the originally trained marginal space deep neural network architecture.

According to various possible embodiments, approximation of the weights for a trained deep neural network (step 1304) can be performed by: a) low rank tensor decompositions; b) approximation through more efficient features; or c) learning weights in separable low spaces directly using sparse approximated weight matrices. The goal of using approximated weight matrices is to maintain the classification performance of the already trained marginal space deep neural network architecture while significantly improving the speed of applying the marginal space deep neural network architecture over the input hypotheses. For example, using separable tensor decomposition in 3D, the computational complexity can be reduced for a volume of $n^3$ voxels filtered/convolved with a kernel $k^3$ voxels from the order of $(k^3 \cdot n^3)$ to the order of $(k \cdot n^3)$. In the context of anatomical object detection, the approximation of the weight matrices in the marginal space deep neural network architecture can be combined with a cascade classifier architecture trained on the already learned image features. The cascade can be trained using greedy incremental feature selection from the first network layer of features and then fine tuning the cascade for close to a 100% true positive rate.

According to a possible embodiment, given an already trained marginal space deep neural network architecture, trained weights can be approximated (step 1304) through low rank tensor factorization methods. It can be noted that in high dimensions, this task is in general NP-hard without guarantees for a globally optimal approximation solution. Accordingly, most low rank tensor factorization approaches are based on iterative optimization of a distance function between the target tensor and its low rank representation. Optimizations focus on either minimizing the two-norm (least squares) error under identically distributed noise or the Kullback-Leibler divergence between the low rank decomposition and the target tensor. Any such method for low rank tensor factorization can be used in order to approximate the learned weights of the trained deep neural networks. In advantageous implementation, the learned tensor weights of each trained deep neural network can be replaced with an approximating decomposition by fixing either the rank or the minimized error of the reconstruction. The approximation of a particular trained deep neural network can be refined iteratively by one of the following procedures: (1) After each full rank training epoch, project each of the tensors in the low rank space and repeat iteratively until the error remains stable; or (2) At each epoch, directly update the weights in the low rank space and repeat iteratively until the error remains stable.

Figure 14:
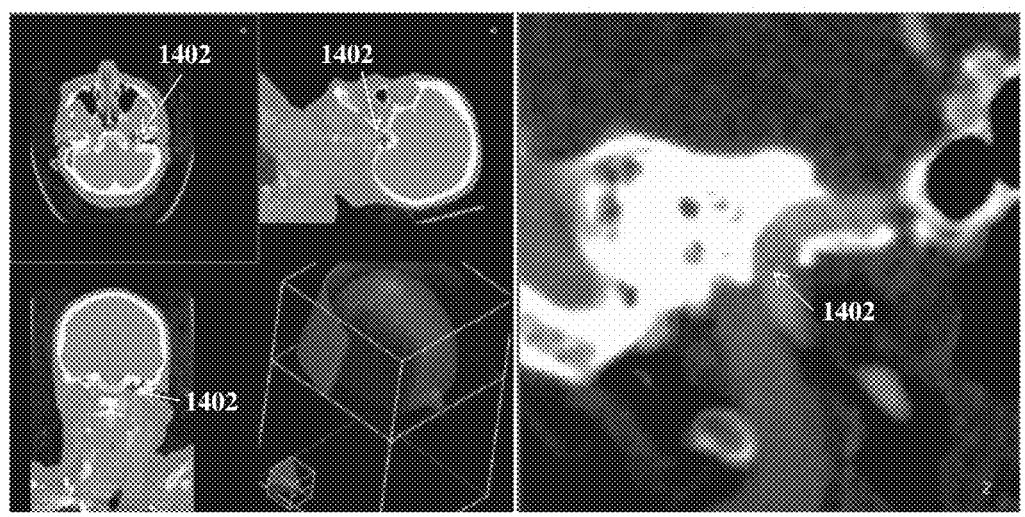
FIG. 14 illustrates exemplary results of landmark detection in a whole body computed tomography (CT) scan using an approximation of a trained marginal space deep neural network architecture.

FIG. 14 illustrates exemplary results of landmark detection in a whole body computed tomography (CT) scan using an approximation of a trained marginal space deep neural network architecture. As shown in FIG. 14, a target vascular landmark 1402 was detected in a whole body CT volume using an approximation of a trained marginal space deep neural network architecture. In the example of FIG. 14, a database of 272 annotated 3D CT volumes from 206 patients was used, with 204 volumes used for training and 68 volumes used for testing. The input box scanned over the image has a size of 20×20×20 mm. A discriminative marginal space deep neural network architecture with convolutional layers was trained with bootstrapping with the following architecture: 1: 6 convolutional layers with 5×5×5 kernels; 2: aggregation layer with 2×2×2 kernel; 3: 6×12 convolutional layers with 5×5×5 kernels; 4: aggregation layer with 2×2×2 kernel; 5: linear classifier layer with two classes. A rank 2 decomposition was used for approximating the weights of the marginal space deep neural network architecture. In this example, the full rank marginal space deep neural network architecture achieved a classifier error on the testing data of 2.0%. The full rank marginal space deep neural network architecture achieved training error with a mean of 1.38 mm, a standard deviation of 0.67 mm, a median of 1.25 mm, and an error at the $80^{th}$ percentile of 1.90 mm. The full rank marginal space deep neural network architecture achieved testing error with a mean of 1.49 mm, a standard deviation of 1.07 mm, a median of 1.32 mm, and an error at the $80^{th}$ percentile of 2.06 mm. The reduced rank approximation of the marginal space deep neural network architecture achieved an approximating classifier error on the testing data of 3.0%. The reduced rank approximation of the marginal space deep neural network architecture achieved training error with a mean of 1.34 mm, a standard deviation of 0.63 mm, a median of 1.28 mm, and an error at the $80^{th}$ percentile of 1.73 mm. The reduced rank approximation of the marginal space deep neural network architecture achieved testing error with a mean of 1.62 mm, a standard deviation of 1.36 mm, a median of 1.36 mm, and an error at the $80^{th}$ percentile of 2.09 mm. Accordingly, the performance of the approximation of the marginal space deep neural network architecture is very similar to that of the full rank marginal space deep neural network architecture. However, the run time of the reduced rank approximation is much faster than that of the full rank marginal space deep neural network architecture.

Marginal Space Deep Learning (MSDL) utilizes deep learning architectures to detect anatomical objects in a series of marginal parameter spaces. However, the direct application of deep learning to volumetric data results in a very high computational complexity. In an advantageous embodiment, sparse deep neural networks are trained to learn representations of from 3D medical image modalities and are used to perform 3D object detection and segmentation in volumetric medical image data. Sparse adaptive deep neural networks are trained by injecting sparsity into deep neural network architectures, which results in a considerable increase in computational efficiency while also serving as regularization and reducing overfitting. Two alternative embodiments for injecting sparsity are described herein, one based on threshold enforcement, adjusted incrementally during the learning process, and another using a robust regularization scheme. In essence, these embodiments replace the uniform sampling pattern used for standard features with an adaptive, self-learned sparse sampling pattern. According to an advantageous embodiment of the present invention, the sparse deep neural networks are integrated into the marginal space deep learning (MSDL) framework described above in connection with FIGS. 1, 4, and 5. In particular, respective sparse deep neural networks can be trained for each of a plurality of marginal search spaces (e.g., position, position-orientation, and position-orientation-scale) and used to segment a 3D anatomical object in an input 3D medical image.

In order to deal with the high computational demands associated with training a 3D deep neural network and applying it for scanning large volumetric spaces, two methods for injecting sparsity during training are described herein. For general notation purposes, the parameters of a convolution filter can be defined as the pair (w,b), where w encodes the weights and b represents the associated bias. The same notation holds for a fully connected layer, which can conceptually be regarded as a convolution layer with the filter size equal to the underlying feature-map size. For training, a batch-wise optimization process using the Stochastic Gradient Descent (SGD) method can be applied.

In one embodiment, threshold enforced sparsity is used to inject sparsity into deep neural network. Threshold enforced sparsity injects sparsity into one or more layers of a deep neural network by using a greedy approach to gradually eliminate low magnitude network connections during the training process. By removing weights with a small absolute value, the affected neurons are able to recover and preserve their output response unchanged and also more invariant and robust. The impact of a sparsity injection procedure is quantified with the parameter p ($0<p<1$). At each stage, for each filter of a considered layer, a proportion of the remaining weights (defined by the value p) is set to zero. If $N_i$ represents the number of preserved (non-zero weights before the i-th stage, then $N_{i+1}=(1-p)N_i$. As such, in the i-th stage, the $pN_i$ weights having the smallest absolute value are eliminated (set to zero). Each stage is completed by a continuation of the training process for a small number of epochs (e.g., 10-20) using only the remaining weights. This allows the neurons to recover from the information loss, and adapt their response based on the remaining incoming connections. To further sustain this recovery, the $L_1$ norm $\|w\|_1$ can be preserved over each injection stage by imposing a re-normalization. In an advantageous implementation, the process is finished when a target sparsity degree (e.g., 95%) is reached. In other words, the training is completed when the fraction $(1-p)^s$, specifying the remaining proportion of coefficients after s stages, reaches the preset target value. The process is finished when the target sparsity is reach (up to 95%). In other words, the training is completed when the fraction $(1-p)^s$, specifying the remaining proportion of coefficients after s stages, reaches the preset target value.

In another embodiment, sparsity is induced in feature kernels of a deep neural network architecture by using a norm-enforcing regularization. In an advantageous implementation, to overcome the computational limitations of the $L_0$-norm while still maintaining its advantages with respect to the underlying sparse penalization scheme, an approximating penalty term called re-weighted $L_1$ norm (RL1) is used. An adapted cost function including the re-weighted $L_1$ norm penalty term is given by: $C(w)=C_0(w)+\Sigma_i^N \lambda_i \|w_i\|$, where $C_0(w)$ is the initial cost function and $\lambda=(\lambda_1, \lambda_2, \ldots \lambda_N)$ are the re-weighting coefficients. By pre-training the network using this norm-enforcing regularization, the magnitude of particular weights can be forced to drop to zero. After this stage, a threshold is enforced, specifying the absolute limit under which the connections are explicitly removed (set to zero). Then, the network is trained until saturation on the remaining weights.

The two sparsity injecting methods described herein emulate in practice the benefits of regularization. By simplifying the network through parameter elimination, individual neurons are forced to learn more robust and effective representations. They become more insensitive to noise and other factors that do not describe the underlying observations. Moreover, the simplification actively prohibits complex neural co-adaptations, reducing the risk of overfitting the underlying training set. Along with all these advantages, the network simplification also considerably boosts the evaluation speed, which is important when scanning large parameter spaces.

A challenge arising with the use of deep neural networks as the discriminating engine in each stage of the marginal space framework, is the high class imbalance. This imbalance can reach ratios of 1:800 positive to negative samples. A deep architecture cannot be trained with an SGD approach on such an unbalanced set and simply re-weighting the penalties for the network cost function further worsens the vanishing gradient effect. Instead, in an advantageous embodiment, a negative filtering cascade of classifiers is used to hierarchically eliminate as many negatives as possible while preserving the positive samples across cascade stages. More specifically, in each stage of the cascade, a simple, shallow, sparse neural network is employed and its decision boundary is tuned to eliminate the maximum number of true negatives. The remaining samples are propagated through to the next cascade stage where the same filtering procedure is repeated, unless a balanced sample set is achieved. In order to train a network within the cascade, we iterate at epoch level over the complete positive sample set, while at each batch level, we randomly sample the negative space to obtain a balanced training batch.

Figure 15:
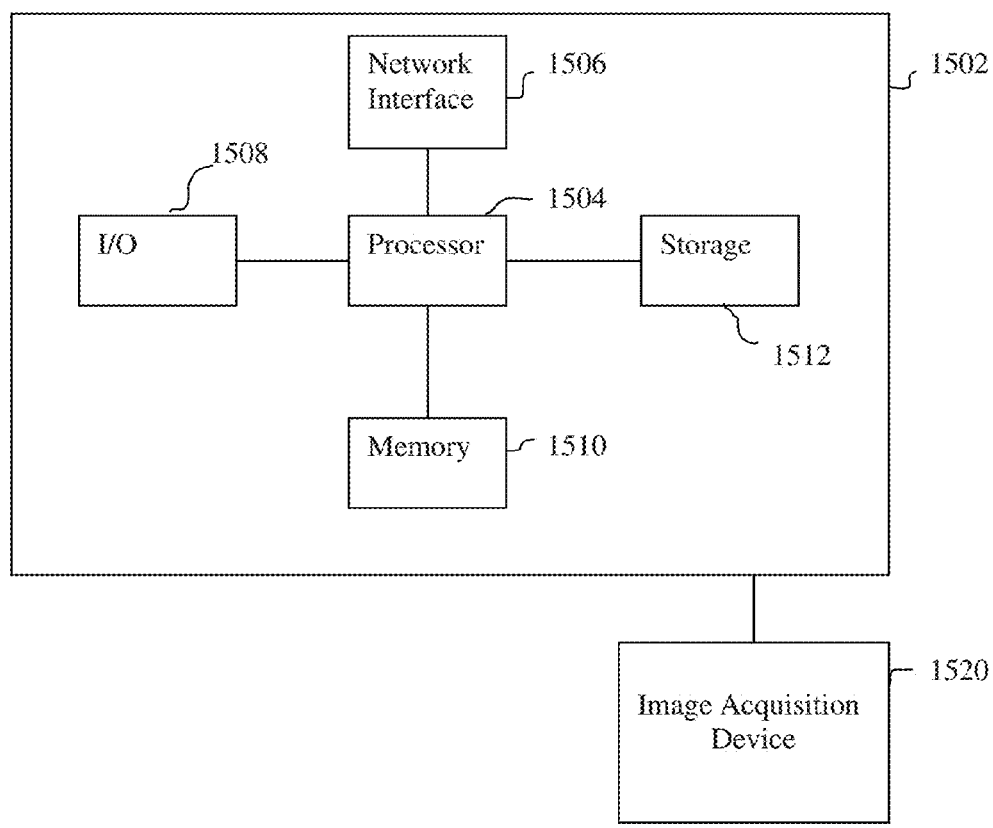
FIG. 15 is a high-level block diagram of a computer capable of implementing the present invention.

The above-described methods for training a series of deep neural networks, anatomical object detection using trained deep neural networks, and anatomical object detection using an approximation of a trained deep neural network architecture can be implemented on a computer using well-known computer processors, memory units, storage devices, computer software, and other components. A high-level block diagram of such a computer is illustrated in FIG. 15. Computer 1502 contains a processor 1504, which controls the overall operation of the computer 1502 by executing computer program instructions which define such operation. The computer program instructions may be stored in a storage device 1512 (e.g., magnetic disk) and loaded into memory 1510 when execution of the computer program instructions is desired. Thus, the steps of the methods of FIGS. 1, 4, 5, 6, 9, and 13 may be defined by the computer program instructions stored in the memory 1510 and/or storage 1512 and controlled by the processor 1504 executing the computer program instructions. An image acquisition device 1520, such as an MR scanning device, CT scanning device, ultrasound device, x-ray image acquisition device, etc., can be connected to the computer 1502 to input image data to the computer 1502. It is possible to implement the image acquisition device 1520 and the computer 1502 as one device. It is also possible that the image acquisition device 1520 and the computer 1502 communicate wirelessly through a network. In a possible embodiment, the computer 1502 may be located remotely from the image acquisition device 1520, and the computer 1502 may perform method steps as part of a server or cloud based service. The computer 1502 also includes one or more network interfaces 1506 for communicating with other devices via a network. The computer 1502 also includes other input/output devices 1508 that enable user interaction with the computer 1502 (e.g., display, keyboard, mouse, speakers, buttons, etc.). Such input/output devices 1508 may be used in conjunction with a set of computer programs as an annotation tool to annotate volumes received from the image acquisition device 1520. One skilled in the art will recognize that an implementation of an actual computer could contain other components as well, and that FIG. 15 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for anatomical object detection in a medical image of a patient, comprising:
   receiving a medical image of a patient including a target anatomical object; and
   detecting a pose of the target anatomical object in the medical image in a series of marginal parameter spaces of increasing dimensionality using a respective trained deep neural network for each of the marginal parameter spaces, wherein each respective trained deep neural network inputs image patches of the medical image, samples pixels or voxels in each input image patch in a sparse sampling pattern adaptively learned during training of the respective trained deep neural network, and operates directly on the pixels or voxels sampled from each input image patch to calculate one or more candidates for the target anatomical object in a respective one of the marginal parameter spaces and wherein, for each of the marginal parameter spaces, a respective cascade of trained shallow sparse neural networks filters image patches of the medical image to remove negative image patches prior to the remaining image patches being input to the respective trained deep neural network for that marginal parameter space.

2. The method of claim 1, wherein the respective trained deep neural network for at least one of the marginal parameter spaces comprises a discriminative deep neural network that inputs hypothesis image patches in the respective marginal parameter space, and calculates, for each of the hypothesis image patch, a probability that the hypothesis image patch is an image patch of the target anatomical object in the respective marginal parameter space.

3. The method of claim 1, wherein the respective trained deep neural network for at least one of the marginal parameter spaces comprises a deep neural network regressor that inputs hypothesis image patches in the respective marginal parameter space, and calculates, for each hypothesis image patch, a displacement vector that maps the hypothesis image patch to a predicted image patch of the target anatomical object in the respective marginal parameter space.

4. The method of claim 3, wherein the deep neural network regressor further calculates, for each hypothesis image patch, a probability for the corresponding predicted image patch of the target anatomical object in the respective marginal parameter space.

5. The method of claim 3, wherein the deep neural network regressor iteratively refines the predicted image patches of the target anatomical object in the respective marginal parameter space by inputting each predicted image patch back into the deep neural network regressor and calculating, for each predicted image patch, a displacement vector that maps the predicted image patch to a refined predicted image patch in the respective marginal parameter space.

6. The method of claim 1, wherein the series of marginal parameter spaces comprises a position parameter space, a position-orientation parameter space, and a position-orientation-scale parameter space.

7. The method of claim 6, wherein detecting a pose of the target anatomical object in the medical image in a series of marginal parameter spaces of increasing dimensionality using a respective trained deep neural network for each of the marginal parameter spaces comprises:
   detecting position candidates in the medical image using a first trained deep neural network that inputs image patches centered at each of a plurality of voxels in the medical image;
   generating position-orientation hypotheses based on the detected position candidates;
   detecting position-orientation candidates in the medical image using a second trained deep neural network that inputs image patches corresponding to the position-orientation hypotheses;
   generating position-orientation-scale hypotheses based on the detected position-orientation candidates; and
   detecting the pose of the target anatomical object in the medical image using a third trained deep neural network that inputs image patches corresponding to the position-orientation-scale hypotheses.

8. The method of claim 7, wherein generating position-orientation hypotheses based on the detected position candidates comprises:
   rotating a respective image patch centered at each detected position candidate to a plurality of orientations sampled from a predetermined range of orientations for the target anatomical object.

9. The method of claim 7, wherein generating position-orientation-scale hypotheses based on the detected position-orientation candidates comprises:
   scaling a respective image patch corresponding to each detected position-orientation candidate to a plurality of scales sampled from a predetermined range of scales for the target anatomical object.

10. The method of claim 7, wherein the second trained deep neural network is a trained deep neural network regressor, and generating position-orientation hypotheses based on the detected position candidates comprises:
   generating a respective position-orientation hypothesis for each detected position candidate by using an image patch centered at each detected position candidate as the respective position-orientation hypothesis.

11. The method of claim 7, wherein the second trained deep neural network is a trained deep neural network regressor, and generating position-orientation-scale hypotheses based on the detected position-orientation candidates comprises:
generating a respective position-orientation-scale hypothesis for each detected position-orientation candidate by using an image patch corresponding to each detected position-orientation candidate as the respective position-orientation-scale hypothesis.

12. The method of claim 1, wherein the respective deep neural network for each of the marginal parameter spaces is a multi-layer deep neural network trained using a stacked denoising auto-encoder (DAE).

13. The method of claim 1, wherein the respective deep neural network for each of the marginal parameter spaces is a multi-layer deep neural network trained using one of a convolutional neural network (CNN), a stacked restricted Boltzmann machine (RBM), or a stacked auto-encoder (AE).

14. The method of claim 1, wherein the respective trained deep neural network for each of the marginal parameter spaces is trained by sequentially training each of a plurality of hidden layers to reconstruct respective inputs to each hidden layer in an unsupervised pre-training stage, and training the deep neural network to detect the target anatomical object in the respective marginal parameter space based on ground truth training image patches in the respective marginal parameter space in a supervised training stage.

15. The method of claim 14, wherein the respective trained deep neural network for each of the marginal parameter spaces is trained in the supervised training stage by adding an output layer for a target output for the respective marginal parameter space and training the plurality of hidden layers and the output layer using back-propagation to minimize an error between detected image patches for the anatomical object and the ground truth training image patches in the respective marginal parameter space.

16. The method of claim 14, wherein the respective trained deep neural network for each of the marginal parameter spaces is trained in the supervised training stage by treating an output of the plurality of hidden layers as high-level image features and training a discriminative classifier based on the high-level image features output by the plurality of hidden layers.

17. The method of claim 1, wherein the trained deep neural network for a first one of the marginal parameter spaces is trained using training image patches sampled from a set of training images, and the trained deep neural network for each subsequent one of the marginal parameter spaces is trained using training image patches generated by augmenting training image patches detected by the trained deep neural network in a preceding marginal parameter space with additional parameters of a current marginal parameter space sampled from a range of the current marginal parameter space in the training images.

18. The method of claim 1, wherein detecting a pose of the target anatomical object in the medical image in a series of marginal parameter spaces of increasing dimensionality using a respective trained deep neural network for each of the marginal parameter spaces comprises:
for at least one of the marginal parameter spaces:
calculating an approximation of the respective trained deep neural network for that marginal parameter space; and
detecting one or more candidates for the target anatomical object in that marginal parameter space using the approximation of the respective trained deep neural network for that marginal parameter space.

19. The method of claim 18, wherein calculating an approximation of the respective trained deep neural network for that marginal parameter space comprises:
calculating a reduced rank approximation of trained weights of the respective trained deep neural network for that marginal parameter space.

20. The method of claim 19, wherein calculating a reduced rank approximation of trained weights of the respective trained deep neural network for that marginal parameter space comprises:
calculating a low rank tensor decomposition to approximate the trained weights of the respective trained deep neural network for that marginal parameter space.

21. The method of claim 19, wherein calculating a reduced rank approximation of trained weights of the respective trained deep neural network for that marginal parameter space comprises:
approximating the trained weights of the respective trained deep neural network for that marginal parameter space using a sparse approximation matrix.

22. An apparatus for anatomical object detection in a medical image of a patient, comprising:
a processor; and
a memory storing computer program instructions which when executed by the processor cause the processor to perform operations comprising:
receiving a medical image of a patient including a target anatomical object; and
detecting a pose of the target anatomical object in the medical image in a series of marginal parameter spaces of increasing dimensionality using a respective trained deep neural network for each of the marginal parameter spaces, wherein each respective trained deep neural network inputs image patches of the medical image, samples pixels or voxels in each input image patch in a sparse sampling pattern adaptively learned during training of the respective trained deep neural network, and operates directly on the pixels or voxels sampled from each input image patch to calculate one or more candidates for the target anatomical object in a respective one of the marginal parameter spaces, and wherein, for each of the marginal parameter spaces, a respective cascade of trained shallow sparse neural networks filters image patches of the medical image to remove negative image patches prior to the remaining image patches being input to the respective trained deep neural network for that marginal parameter space.

23. The apparatus of claim 22, wherein the respective trained deep neural network for at least one of the marginal parameter spaces comprises a discriminative deep neural network that inputs hypothesis image patches in the respective marginal parameter space, and calculates, for each of the hypothesis image patch, a probability that the hypothesis image patch is an image patch of the target anatomical object in the respective marginal parameter space.

24. The apparatus of claim 22, wherein the respective trained deep neural network for at least one of the marginal parameter spaces comprises a deep neural network regressor that inputs hypothesis image patches in the respective marginal parameter space, and calculates, for each hypothesis image patch, a displacement vector that maps the hypothesis image patch to a predicted image patch of the target anatomical object in the respective marginal parameter space.

25. The apparatus of claim 24, wherein the deep neural network regressor further calculates, for each hypothesis image patch, a probability for the corresponding predicted image patch of the target anatomical object in the respective marginal parameter space.

26. The apparatus of claim 24, wherein the deep neural network regressor iteratively refines the predicted image patches of the target anatomical object in the respective marginal parameter space by inputting each predicted image patch back into the deep neural network regressor and calculating, for each predicted image patch, a displacement vector that maps the predicted image patch to a refined predicted image patch in the respective marginal parameter space.

27. The apparatus of claim 22, wherein the series of marginal parameter spaces comprises a position parameter space, a position-orientation parameter space, and a position-orientation-scale parameter space.

28. The apparatus of claim 27, wherein detecting a pose of the target anatomical object in the medical image in a series of marginal parameter spaces of increasing dimensionality using a respective trained deep neural network for each of the marginal parameter spaces comprises:
  detecting position candidates in the medical image using a first trained deep neural network that inputs image patches centered at each of a plurality of voxels in the medical image;
  generating position-orientation hypotheses based on the detected position candidates;
  detecting position-orientation candidates in the medical image using a second trained deep neural network that inputs image patches corresponding to the position-orientation hypotheses;
  generating position-orientation-scale hypotheses based on the detected position-orientation candidates; and
  detecting the pose of the target anatomical object in the medical image using a third trained deep neural network that inputs image patches corresponding to the position-orientation-scale hypotheses.

29. The apparatus of claim 22, wherein the respective deep neural network for each of the marginal parameter spaces is a multi-layer deep neural network trained using a stacked denoising auto-encoder (DAE).

30. The apparatus of claim 22, wherein the respective deep neural network for each of the marginal parameter spaces is a multi-layer deep neural network trained using one of a convolutional neural network (CNN), a stacked restricted Boltzmann machine (RBM), or a stacked auto-encoder (AE).

31. The apparatus of claim 22, wherein the respective trained deep neural network for each of the marginal parameter spaces is trained by sequentially training each of a plurality of hidden layers to reconstruct respective inputs to each hidden layer in an unsupervised pre-training stage, and training the deep neural network to detect the target anatomical object in the respective marginal parameter space based on ground truth training image patches in the respective marginal parameter space in a supervised training stage.

32. The apparatus of claim 31, wherein the respective trained deep neural network for each of the marginal parameter spaces is trained in the supervised training stage by adding an output layer for a target output for the respective marginal parameter space and training the plurality of hidden layers and the output layer using back-propagation to minimize an error between detected image patches for the anatomical object and the ground truth training image patches in the respective marginal parameter space.

33. The apparatus of claim 31, wherein the respective trained deep neural network for each of the marginal parameter spaces is trained in the supervised training stage by treating an output of the plurality of hidden layers as high-level image features and training a discriminative classifier based on the high-level image features output by the plurality of hidden layers.

34. The apparatus of claim 22, wherein the trained deep neural network for a first one of the marginal parameter spaces is trained using training image patches sampled from a set of training images, and the trained deep neural network for each subsequent one of the marginal parameter spaces is trained using training image patches generated by augmenting training image patches detected by the trained deep neural network in a preceding marginal parameter space with additional parameters of a current marginal parameter space sampled from a range of the current marginal parameter space in the training images.

35. The apparatus of claim 22, wherein detecting a pose of the target anatomical object in the medical image in a series of marginal parameter spaces of increasing dimensionality using a respective trained deep neural network for each of the marginal parameter spaces comprises:
  calculating an approximation of the respective trained deep neural network for at least one of the marginal parameter spaces; and
  detecting one or more candidates for the target anatomical object in the at least one of the marginal parameter spaces using the approximation of the respective trained deep neural network for the at least one of the marginal parameter spaces.

36. The apparatus of claim 35, wherein calculating an approximation of the respective trained deep neural network for at least one of the marginal parameter spaces comprises:
  calculating a reduced rank approximation of trained weights of the respective trained deep neural network for the at least one of the marginal parameter spaces.

37. A non-transitory computer readable medium storing computer program instructions for anatomical object detection in a medical image of a patient, the computer program instructions when executed by a processor cause the processor to perform operations comprising:
  receiving a medical image of a patient including a target anatomical object; and
  detecting a pose of the target anatomical object in the medical image in a series of marginal parameter spaces of increasing dimensionality using a respective trained deep neural network for each of the marginal parameter spaces, wherein each respective trained deep neural network inputs image patches of the medical image, samples pixels or voxels in each input image patch in a sparse sampling pattern adaptively learned during training of the respective trained deep neural network, and operates directly on the pixels or voxels sampled from each input image patch to calculate one or more candidates for the target anatomical object in a respective one of the marginal parameter spaces, and wherein, for each of the marginal parameter spaces, a respective cascade of trained shallow sparse neural networks filters image patches of the medical image to remove negative image patches prior to the remaining image patches being input to the respective trained deep neural network for that marginal parameter space.

38. The non-transitory computer readable medium of claim 37, wherein the respective trained deep neural network for at least one of the marginal parameter spaces comprises a discriminative deep neural network that inputs hypothesis image patches in the respective marginal parameter space, and calculates, for each of the hypothesis image patch, a probability that the hypothesis image patch is an image patch of the target anatomical object in the respective marginal parameter space.

39. The non-transitory computer readable medium of claim 37, wherein the respective trained deep neural network for at least one of the marginal parameter spaces comprises a deep neural network regressor that inputs hypothesis image patches in the respective marginal parameter space, and calculates, for each hypothesis image patch, a displacement vector that maps the hypothesis image patch to a predicted image patch of the target anatomical object in the respective marginal parameter space.

40. The non-transitory computer readable medium of claim 39, wherein the deep neural network regressor further calculates, for each hypothesis image patch, a probability for the corresponding predicted image patch of the target anatomical object in the respective marginal parameter space.

41. The non-transitory computer readable medium of claim 39, wherein the deep neural network regressor iteratively refines the predicted image patches of the target anatomical object in the respective marginal parameter space by inputting each predicted image patch back into the deep neural network regressor and calculating, for each predicted image patch, a displacement vector that maps the predicted image patch to a refined predicted image patch in the respective marginal parameter space.

42. The non-transitory computer readable medium of claim 37, wherein the series of marginal parameter spaces comprises a position parameter space, a position-orientation parameter space, and a position-orientation-scale parameter space.

43. The non-transitory computer readable medium of claim 42, wherein detecting a pose of the target anatomical object in the medical image in a series of marginal parameter spaces of increasing dimensionality using a respective trained deep neural network for each of the marginal parameter spaces comprises:
  detecting position candidates in the medical image using a first trained deep neural network that inputs image patches centered at each of a plurality of voxels in the medical image;
  generating position-orientation hypotheses based on the detected position candidates;
  detecting position-orientation candidates in the medical image using a second trained deep neural network that inputs image patches corresponding to the position-orientation hypotheses;
  generating position-orientation-scale hypotheses based on the detected position-orientation candidates; and
  detecting the pose of the target anatomical object in the medical image using a third trained deep neural network that inputs image patches corresponding to the position-orientation-scale hypotheses.

44. The non-transitory computer readable medium of claim 43, wherein generating position-orientation hypotheses based on the detected position candidates comprises:
  rotating a respective image patch centered at each detected position candidate to a plurality of orientations sampled from a predetermined range of orientations for the target anatomical object.

45. The non-transitory computer readable medium of claim 43, wherein generating position-orientation-scale hypotheses based on the detected position-orientation candidates comprises:
  scaling a respective image patch corresponding to each detected position-orientation candidate to a plurality of scales sampled from a predetermined range of scales for the target anatomical object.

46. The non-transitory computer readable medium of claim 43, wherein the second trained deep neural network is a trained deep neural network regressor, and generating position-orientation hypotheses based on the detected position candidates comprises:
  generating a respective position-orientation hypothesis for each detected position candidate by using an image patch centered at each detected position candidate as the respective position-orientation hypothesis.

47. The method non-transitory computer readable medium claim 43, wherein the second trained deep neural network is a trained deep neural network regressor, and generating position-orientation-scale hypotheses based on the detected position-orientation candidates comprises:
  generating a respective position-orientation-scale hypothesis for each detected position-orientation candidate by using an image patch corresponding to each detected position-orientation candidate as the respective position-orientation-scale hypothesis.

48. The non-transitory computer readable medium of claim 37, wherein the respective deep neural network for each of the marginal parameter spaces is a multi-layer deep neural network trained using a stacked denoising auto-encoder (DAE).

49. The non-transitory computer readable medium of claim 37, wherein the respective deep neural network for each of the marginal parameter spaces is a multi-layer deep neural network trained using one of a convolutional neural network (CNN), a stacked restricted Boltzmann machine (RBM), or a stacked auto-encoder (AE).

50. The non-transitory computer readable medium of claim 37, wherein the respective trained deep neural network for each of the marginal parameter spaces is trained by sequentially training each of a plurality of hidden layers to reconstruct respective inputs to each hidden layer in an unsupervised pre-training stage, and training the deep neural network to detect the target anatomical object in the respective marginal parameter space based on ground truth training image patches in the respective marginal parameter space in a supervised training stage.

51. The non-transitory computer readable medium of claim 50, wherein the respective trained deep neural network for each of the marginal parameter spaces is trained in the supervised training stage by adding an output layer for a target output for the respective marginal parameter space and training the plurality of hidden layers and the output layer using back-propagation to minimize an error between detected image patches for the anatomical object and the ground truth training image patches in the respective marginal parameter space.

52. The non-transitory computer readable medium of claim 50, wherein the respective trained deep neural network for each of the marginal parameter spaces is trained in the supervised training stage by treating an output of the plurality of hidden layers as high-level image features and training a discriminative classifier based on the high-level image features output by the plurality of hidden layers.

53. The non-transitory computer readable medium of claim 37, wherein the trained deep neural network for a first one of the marginal parameter spaces is trained using training image patches sampled from a set of training images, and the trained deep neural network for each subsequent one of the marginal parameter spaces is trained using training image patches generated by augmenting training image patches detected by the trained deep neural network in a preceding marginal parameter space with additional parameters of a current marginal parameter space sampled from a range of the current marginal parameter space in the training images.

54. The non-transitory computer readable medium of claim 37, wherein detecting a pose of the target anatomical object in the medical image in a series of marginal parameter spaces of increasing dimensionality using a respective trained deep neural network for each of the marginal parameter spaces comprises:

for at least one of the marginal parameter spaces:
calculating an approximation of the respective trained deep neural network for that marginal parameter space; and
detecting one or more candidates for the target anatomical object in that marginal parameter space using the approximation of the respective trained deep neural network for that marginal parameter space.

55. The non-transitory computer readable medium of claim 54, wherein calculating an approximation of the respective trained deep neural network for that marginal parameter space comprises:
calculating a reduced rank approximation of trained weights of the respective trained deep neural network for that marginal parameter space.

56. The non-transitory computer readable medium of claim 55, wherein calculating a reduced rank approximation of trained weights of the respective trained deep neural network for that marginal parameter space comprises:
calculating a low rank tensor decomposition to approximate the trained weights of the respective trained deep neural network for that marginal parameter space.

57. The non-transitory computer readable medium of claim 55, wherein calculating a reduced rank approximation of trained weights of the respective trained deep neural network for that marginal parameter space comprises:
approximating the trained weights of the respective trained deep neural network for that marginal parameter space using a sparse approximation matrix.

* * * * *